United States Patent [19]
Rotstein et al.

[11] Patent Number: 5,994,402
[45] Date of Patent: Nov. 30, 1999

[54] ANTI-INFLAMMATORY AND ANTI-PYRETIC METHOD

[76] Inventors: Ori D. Rotstein, 14 Bennington Hts. Dr., Toronto, Ontario, Canada, M4S 1A6; Avery B. Nathens, 87 Flaming Roseway, North York, Ontario, Canada, M2N 5W8

[21] Appl. No.: 08/796,292

[22] Filed: Feb. 7, 1997

Related U.S. Application Data

[60] Provisional application No. 60/019,361, Jun. 5, 1996.

[51] Int. Cl.[6] .................................................. A61K 31/225
[52] U.S. Cl. ......................... 514/547; 514/549; 514/675; 514/562
[58] Field of Search .................................... 514/547, 549, 514/675, 562

[56] References Cited

U.S. PATENT DOCUMENTS

| | | | |
|---|---|---|---|
| 5,047,395 | 9/1991 | Wu | 514/2 |
| 5,171,885 | 12/1992 | Griffith et al. | 562/556 |
| 5,340,813 | 8/1994 | Klein et al. | 514/263 |

OTHER PUBLICATIONS

Chemical ABstracts AN 1995:359261, Imamura et al., Jan. 1995.
Medline abstract AN 95156233, Grattagliano et al., Jan. 1995.
Sznajder JI, et al., "Increased hydrogen peroxide in the expired breath of patients with acute hypoxemic respiratory failure." *Chest*, 96:606–612 (1989).
Cochrane CG, et al., "Pathogenesis of the adult respiratory distress syndrome: evidence of oxidant activity in bronchoalveolar lavage fluid." *J Clin Invest*, 71:754–758 (1983).
Pacht ER, et al., "Deficiency of alveolar lining fluid glutathione in patients with sepsis and the adult respiratory distress syndrome." *Chest*, 100:1397–1403 (1991).
Leff JA, et al., "Postinsult treatment with N–acetylcysteine decreases IL–1 induced neutrophil influx and lung leak in rats." *Am J Physiol*, 265:L501–L506 (1993).
Hybertson BM, et al., "Effect of vitamin E deficiency and supercritical fluid aerosolized vitamin E supplementation on interleukin–1 induced oxidative lung injury in rats." *Free Radic Biol Med*, 537–542 (1995).
Suter PM, et al., "N–acetylcysteine enhances recovery from acute lung injury in man." *Chest*, 105:190–194 (1994).
Knight PR, et al., "The role of neutrophils, oxidants, and proteases in the pathogenesis of acid pulmonary injury." *Anesthesiology*, 77:772–778 (1992).
Gossage JR, et al., "Neutrophil elastase inhibitors, SC–37698 and SC–39026, reduce endotoxin–induced lung dysfunction in awake sheep." *Am Rev Resp Dis*, 147:1371–1379 (1993).
Kanner SB, et al., "Sulfhydryl oxidation down–regulates T–cell signaling and inhibits tyrosine phosphorylation of phospholipase C–g–1." *Proc Natl Acad Sci USA*, 89:300–304 (1992).
Meyer M, et al., "$H_2O_2$ and antioxidants have opposite effects on activation of NF–kB and AP–1 in intact cells: AP–1 as secondary antioxidant–responsive factor." *EMBO J*, 12:2005–2015 (1993).
Malter JS, Hong Y, "A redox switch and phosphorylation are involved in the post translational up–regulation of the adenosine–uridine binding factor by phorbol ester and ionophore." *J Biol Chem*, 266:3167–3171 (1991).
Meister A, "Glutathione deficiency produced by inhibition of its synthesis, and its reversal: applications in research and therapy." *Pharmac Ther*, 51:155–194 (1991).
Vanella A, et al., "Free radical scavenger depletion in post–ischemic reperfusion brain damage." *Neurochem Res* 18:1337–1340 (1993).
Tiegs G, et al., "Leukotriene–mediated liver injury." *Biochem Pharmacol*, 37:2569–2573 (1988).
Atzori L, et al., "Thiol modification in $H_2O_2$ and thromboxane induced vaso– and bronchoconstriction in rat perfused lung." *J Appl Physiol*, 71:1309–1314 (1991).
Chemical Abstracts AN 1994:235946, Miranda et al, 1994.
Chemical Abstracts, AN 1985:199061, Tsan et al, 1985.

*Primary Examiner*—Keith D. MacMillan
*Attorney, Agent, or Firm*—Viviana Amzel; Pretty, Schroeder & Poplawski

[57] ABSTRACT

A method of reducing or inhibiting inflammation and inducing or promoting anti-pyresis comprises administering to a mammal in need of such treatment, an amount of a glutathione depleting agent effective to reduce or inhibit neutrophil sequestration at the inflammation site. The agent may be administered as a pharmaceutical composition including a carrier. Examples of the agent itself are diethylmaleate (DEM), phorone, buthionine-sulfoximine (BSO), glutathione depleting diethylmaleate (DEM) mimetics, glutathione depleting phorone mimetics and glutathione depleting buthionine sulfoximine (BSO) mimetics.

28 Claims, 22 Drawing Sheets

C)

B)

A)

ICAM-1 Northern Blot

LPS  −  +  +
DEM  −  −  +

NF-κB EMSA

LPS  −  −  +  +
DEM  −  +  −  +   comp

The Effect of DEM on Survival

ANTI-INFLAMMATORY AND ANTI-PYRETIC METHOD

This application is a Continuation-in-part of U.S. Provisional application Ser. No. 60/019,361, entitled, "ANTI-INFLAMMATORY AGENT," by the same inventors filed on Jun. 5, 1996.

BACKGROUND OF THE INVENTION

The neutrophil plays a critical role in the pathogenesis of the Adult Respiratory Distress Syndrome (ARDS), as strategies aimed at preventing neutrophil sequestration in the lung, such as neutrophil depletion or administration of antibody directed against adhesion molecules, attenuate lung injury in experimental models. Further, neutrophil-mediated oxidative damage to the alveolocapillary unit is thought to be necessary for the full expression of the syndrome in the majority of cases. The association between oxidative stress and ARDS is suggested by the presence of increases in expired $H_2O_2$ [1] as well as an increase in oxidant levels [2] and a reduction in reduced glutathione (GSH) [3] in bronchoalveolar lavage fluid (BALF) obtained from patients with ARDS.

Despite this association, there are relatively few studies demonstrating benefit following administration of exogenous antoxidants in animal models of acute lung injury caused by inflammatory stimuli [4,5], and only one study in man demonstrating marginal efficacy in patients at risk for ARDS [6]. These data indicate that oxidant-mediated tissue injury per se may not be the only mechanism whereby the inflammatory process leading to ARDS is initiated. For example, proteases [7] and elastases [8] are released by activated neutrophils and contribute to lung injury, suggesting that greater success at attenuating lung injury may be achieved not only through improving antioxidant defenses, but by limiting cell activation. In this regard, there is accumulating evidence that alterations in the cellular redox state play a critical role in cell signaling through modulation of tyrosine phosphorylation [9], regulation of transcription [10], and alterations in messenger RNA stability [11], suggesting that administration of antioxidants or sulfhydryl-reactive agents may have important modulatory effects on cell activation. GSH is the most abundant intracellular thiol and maintains the intracellular redox state through detoxification of oxidized moieties as a result of the activity of glutathione peroxidase, glutathione S-transferase, and a direct oxidant scavenging effect [12]. Several recent studies have demonstrated paradoxical beneficial effects associated with GSH depletion, including improved survival following cerebral ischemia-reperfusion [13], abrogation of hepatic injury following systemic endotoxemia [14], and a reduction in lung injury following the administration of either oxidants or thromboxane in an ex vivo, isolated-perfused model of lung injury [15]. The mechanism(s) underlying this protection remains unclear.

SUMMARY OF THE INVENTION

The present invention relates to the effect of GSH depletion by diethylmaleate (DEM) following endotoxin (LPS)-induced acute lung injury. Altering the redox state of the cell by intracellular thiol depletion attenuates the local inflammatory response, and thus prevents injury. The invention demonstrates that a thiol depleting agent, diethylmaleate, abrogates lung injury by means of an alteration in neutrophil-endothelial interactions with a resultant reduction in lung PMN sequestration This invention relates to a method of preventing damage to a patient by inflammatory stimuli by administering an exogenous agent which alters the redox state of the cell The agent prevents damage to a cell, organ or tissue of a patient The agent is a thiol depleting agent. In one case, the thiol depleting agent is selected from a group consisting of diethylmaleate (DEM), phorone and buthionine sulfoximine (BSO). In another case, the thiol depleting agent is a mimetic of a compound selected from a group consisting of diethylmaleate (DEM), phorone and buthionine sulfoximine (BSO). In another case, the thiol depleting agent comprises all or part of a region of a compound selected from a group consisting of diethylmaleate (DEM) or a mimetic of DEM having thiol depleting activity, phorone, a mimetic of phorone having thiol depleting activity, buthionine sulfoximine (BSO) and a mimetic of buthionine sulfoximine (BSO) having thiol depleting activity. The route of administration of the agent can include oral administration, parenteral administration, cavity administration, rectal administration, air passage administration. The agent can be administered before or after inflammatory stimuli.

This invention includes a human tissue having an exogenous agent which is a thiol depleting agent. It also includes a human cell having an exogenous agent which is a thiol depleting agent. It includes a human organ having an exogenous agent which is a thiol depleting agent.

The thiol depleting agent of this invention is for the new use of treating a cell, tissue or organ to prevent damage caused by inflammatory stimuli. The agent prevents damage to a cell, organ, tissue of a patient. In one case, the agent is selected from a group consisting of diethylmaleate (DEM), phorone and buthionine sulfoximine (BSO). In another case, the agent is a mimetic of a compound from the group of diethylmaleate (DEM), phorone and buthionine sulfoximine (BSO). In another case, the thiol depleting agent is a mimetic of a compound selected from a group consisting of diethylmaleate (DEM), phorone and buthionine sulfoximine (BSO). In another case, the thiol depleting agent comprises all or part of a region of a compound selected from a group consisting of diethylmaleate (DEM) or a mimetic of DEM having thiol depleting activity, phorone, a mimetic of phorone having thiol depleting activity, buthionine sulfoximine (BSO) and a mimetic of buthionine sulfoximine (BSO) having thiol depleting activity.

The invention includes a pharmaceutical which comprises a thiol depleting agent as the active ingredient together with inert solid or liquid carriers or diluents and, optionally, with additives for pharmaceutical use.

The invention also includes a method of preventing damage to a patient by inflammatory stimuli by administering a thiol depleting agent that adversely and selectively affects the expression of ICAM-1 to alter the redox state of the cell. In one embodiment of the invention, the agent is selected from a group consisting of diethylmaleate (DEM), phorone and buthionine sulfoximine (BSO). in another case, the agent comprises all or part of a region of a compound from the group of diethylmaleate (DEM) or a mimetic of DEM having thiol depleting activity, phorone, a mimetic of phorone having thiol depleting activity, buthionine sulfoximine (BSO) and a mimetic of buthionine sulfoximine (BSO) having thiol depleting activity.

BRIEF DESCRIPTION OF THE DRAWINGS

The following figures illustrate embodiments of the invention.

DETAILED DESCRIPTION OF THE INVENTION

Figure 1:
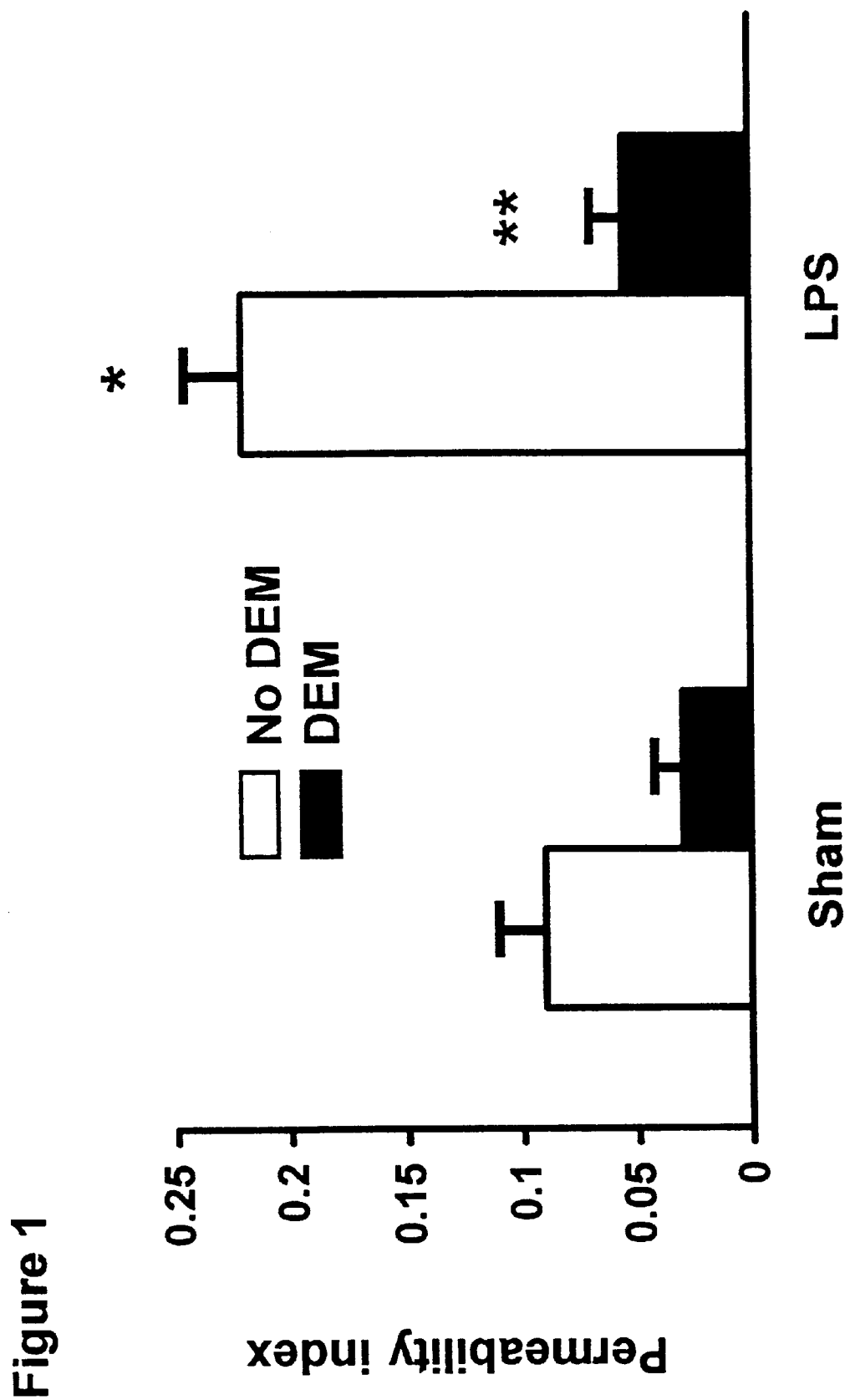
FIG. 1. Pulmonary transcapillary albumin transit was used as a measure of lung injury and was assessed as described in methods. Animals were pretreated with diethylmaleate (6 mmole/kg) or saline one hour prior to intratracheal endotoxin (500 mg) or vehicle challenge and sacrificed 4 hours later. Data are expressed as mean±SEM of at least 4 animals per group. *$p<0.001$ vs sham, **$p<0.001$ vs endotoxin, no diethylmaleate.

The present studies demonstrate that the thiol depleting agent, diethylmaleate markedly reduces the magnitude of lung injury in an experimental model of ARDS induced by intratracheal instillation of LPS. The effect of DEM is present when administered as many as three hours prior to LPS and is also evident when given after LPS treatment. The data suggest that the protective effect is related primarily to the ability of DEM to prevent leukosequestration in the pulmonary vascular bed. Specifically, both histologic evaluation and BALF indicate markedly reduced numbers of PMN. The failure to sequester relates neither to a reduction in PMN CD11b expression or the inability of the neutrophils to migrate. Further, TNF-a levels in BALF are unaffected, suggesting that the initiation of the inflammatory response and availability of chemotactic stimuli were normal. Chemiluminescence was significantly reduced, albeit only to a moderate extent. While this may contribute to an attenuation in the severity of lung injury, a reduction in lung neutrophil sequestration appears to be of far greater importance. Both in vivo and in vitro evidence show that the principal effect of DEM is through modulation of ICAM-1 upregulation. In vitro studies confirm that this is a direct effect of diethylmaleate and not due to cytotoxicity of this agent on the endothelium. Finally, Northern analysis using a specific ICAM-1 cDNA probe suggests that this effect is mediated at the level of ICAM-1 mRNA expression.

ICAM-1 is the most important ligand for the CD11b/CD18 leukocyte adhesion glycoprotein complex and mediates firm adhesion of the neutrophil to the endothelial cell. This interaction is a prerequisite for neutrophil transmigration into the interstitium [27]. Lung neutrophil sequestration has been reported to be ICAM-1 dependent in a variety of animal models, including thermal injury [25], local and distant reperfusion injury [28,29], immune complex deposition [30], as well as following direct administration of TNF-a [26,31]. Thus, it follows that modulation of pulmonary ICAM-1 expression would attenuate endotoxin-induced lung injury. DEM has been reported to be protective following endotoxin/galactosamine induced hepatic necrosis, another model in which neutrophil mediated damage is considered to be of pathogenic significance [14]. Although the mechanism for hepatic protection has not been elucidated, neutrophil influx and hepatic necrosis have recently been demonstrated to be ICAM-1 dependent [32,33] and provide a mechanistic explanation for this observation.

Northern analysis of total lung RNA demonstrates that DEM mediates its effect through a reduction in ICAM-1 mRNA expression. Attenuation of ICAM-1 mRNA expression is not due to a global effect on cell activation or transcription, as BALF TNF-a levels are unaffected. ICAM-1 mRNA expression is regulated at both the level of transcription and through modulation of mRNA stability [34,35]. Several sulfhydryl-reactive agents have been reported to irreversibly inactivate a critical mRNA binding protein implicated in stabilizing ICAM-1 mRNA following cell activation [11,36]. DEM downregulates ICAM-1 mRNA expression via this mechanism, and in doing so abrogates lung PMN sequestration in response to intratracheal LPS.

Examples 11 to 17 also demonstrate that pharmacologic agents characterized by their ability to deplete intracellular thiols are able to reduce the magnitude of lung injury in an experimental model of ARDS induced by the intratracheal administration of endotoxin. The major histopathologic correlate of this effect was the presence of reduced PMN sequestration as evidenced by lung histology and levels of total lung MPO activity. This finding suggested that these agents might act by inhibiting the PMN-endothelial interactions necessary to initiate the inflammatory process. DEM, phorone and buthionine sulfoximine (BSO) are three thiol depleting agents which are useful in decreasing lung injury caused by ARDS. DEM, phorone and buthionine sulfoximine (BSO) are also useful in preventing damage to a patient by inflammatory stimuli in other types of tissues. We previously showed that PMN $b_2$ integrin upregulation and transmigration in response to chemotactic stimuli was unaffected by thiol depletion. We believe that the salutary effect on lung injury is due to altered endothelial cell activation. Several animal models of lung Injury in which ICAM-1/$b_2$-integrin interactions are prevented by administration of antibodies directed against ICAM-1 demonstrate a marked reduction in PMN influx. We showed that DEM modulates expression of this physiologically relevant ligand. The major observation in the present studies is that DEM treatment prevented ICAM-1 upregulation in response to inflammatory stimuli. In vivo, the rise in ICAM-1 protein and gene expression in the lung induced by LPS was totally abrogated by prior treatment with DEM. This was not a global effect on LPS-induced gene expression, since the rise in lung TNF-a mRNA was unaffected. Further, DEM exerted a similar effect on rat and human endothelial cells in vitro without cytotoxicity or an alteration in barrier function. This finding suggests that these agents might exert their actions directly on endothelial cells in vivo, although it does not rule out the possibility that DEM might inhibit other cells in vivo from releasing cytokines which induce endothelial cell ICAM-1 expression. However, as mentioned above, one candidate mediator, TNF-a, did not differ between untreated and DEM-treated animals at the protein or mRNA level.

ICAM-1 is the most important ligand for the CD11b/CD18 leukocyte adhesion glycoprotein complex and mediates firm adhesion of the PMN to the endothelial cell. This interaction is a prerequisite for PMN transmigration across endothelial cell monolayers in vitro and into the interstitium in vivo. The observed effects of GSH depletion on PMN influx into the lung and peritoneal cavity are thus consistent with the importance of ICAM-1 in these processes. The present data demonstrate that the effect of GSH depletion on ICAM-1 expression and subsequent PMN migration is neither site nor stimulus specific as a similar effect is evident in vitro and in the pulmonary and peritoneal capillary beds.

Two lines of evidence show that the protection by DEM is related to the thiol depleting properties of this agent. First, the effect of DEM correlated with its ability to deplete lung GSH. Specifically, concentrations of DEM able to deplete GSH were protective, while lower concentrations had no effect. Secondly, phorone, an unrelated thiol-depleting agent had a similar protective effect excluding the possibility that the effect was due to a conjugate or metabolite of DEM.

The mechanism whereby thiol depletion might preclude ICAM-1 expression and thus exert its beneficial effect in vivo requires further study. Northern analysis of total lung RNA demonstrates that thiol depletion mediates its effect through a prevention of LPS-induced ICAM-1 mRMA expression. ICAM-1 mRNA expression is regulated at the transcriptional level and by means of regulating the rate of mRNA degradation, both of which are modulated by changes In lntracellular thiol concentrations. The promoter region of ICAM-1 contains a consensus binding motif for NF-κB. Recent evidence suggests that thiol oxidation may regulate NF-κB dependent gene activation at the nuclear level. In the nucleus, thiol oxidation prevents the binding of NF-κB to its DNA binding site by forming mixed disulfides at a redox-reactive cysteine in the DNA binding region of NF-κB, leading to a reduction in NF-κB dependent gene expression.

Alternatively, thiol depletion may play a role in modulating ICAM-1 mRNA stability. The 3' untranslated region of ICAM-1 mRNA has several reiterations of the pentamer adenosine-uridine-uridine-uridine-adenosine (AUUUA). This adenosine-uridine rich element (ARE) is a relatively well conserved motif in several labile transcripts. Recently several trans-acting mRNA binding proteins that interact with the ARE have been identified. The binding activity of AU binding factors may either proportionally or inversely correlate with transcript stability. Further, the binding of AUBF to ARE may be modulated by critical thiol groups at the mRNA binding site. A reduction in ICAM-1 mRNA stability mediated via this mechanism may account for a reduction in steady state ICAM-1 mRNA observed following thiol depletion.

One other possible mechanism may relate to an indirect effect on ICAM-1 through altering expression of other mediators or molecules normally upregulated during the inflammatory response. For example, GSH depletion inhibits nitric oxide synthesis through the prevention of inducible nitric oxide synthase gene activation, whereas heat shock protein expression is potentiated. The effects of these and other mediators/molecules on ICAM-1 expression is currently unknown.

The profound reduction in lung neutrophil sequestration animals pretreated with DEM suggests that this agent may have additional effects on PMN-endothelial interactions apart from the effect on ICAM-1 expression demonstrated in the present studies. For example, recent data suggest that thiol oxidizing agents may alter lymphocyte CD11a/CD18 interactions through conformational changes in the $b_2$ integrin. Alternatively, DEM may have additional effects on other endothelial cell adhesion molecules involved in lung leukosequestration including E-selectin and VCAM.

A limited number of other studies have demonstrated beneficial effects associated with GSH depletion, although the mechanism for these effects were not evaluated. Both buthionine sulfoximine (BSO), an agent which prevents de novo GSH synthesis, and DEM reduced mortality following cerebral ischemia-reperfusion injury, while thiol depletion has been reported to be protective in a murine model of endotoxin/galactosamine induced hepatic necrosis. The common pathogenetic link between these models of injury and LPS-induced lung injury in the present studies is the central role of PMN-endothelial cell interactions leading to PMN sequestration and target organ injury. The present studies provide sound evidence that the salutary effect observed in each model is related to impaired upregulation of endothelial adhesion molecules. Importantly, this information shows that treatment with thiol-depleting agents is generally effective in pathologic processes mediated by endothelial cell-PMN interactions involving ICAM-1, a phenomenon demonstrated by the abrogation of thioglycollate-elicited PMN influx into the peritoneal cavity in animals pretreated with DEM in the current study.

There is increasing evidence to suggest that alterations in the redox state of the cell modulates cellular and gene activation. The data presented herein demonstrate that cellular redox manipulation mediated by alterations in intracellular thiol levels is useful in modulating the inflammatory response in disease processes as diverse as acute lung injury to rheumatoid arthritis. These data show that redox manipulation is most effective if directed towards the modulation of cell activation rather than post-hoc attempts at minimizing PMN-mediated oxidative injury by administering exogenous antioxidants—an approach that has demonstrated very little success in man.

As discussed above, intracellular thiol depletion has been reported to modulate mRNA expression of a number of elements implicated in inflammatory processes, including inducible nitric oxide synthase [37,38] and heat shock proteins [39]. Moreover, this study, as well as others [40,41] have demonstrated a reduction in neutrophil oxidant production following thiol depletion. Although the teleologic importance of these thiol-mediated regulatory mechanisms are unclear, reductions in thiol levels have been demonstrated in critically ill patients with ARDS [3] and serve to downregulate uncontrolled inflammation. Further, attempts at augmenting thiol levels in these patients in an attempt to scavenge neutrophil-derived oxidants, have met with little success [6], and may even increase the incidence of adverse outcome [42].

This invention demonstrates that GSH depletion using DEM abrogates LPS-induced lung injury through inhibition of lung PMN sequestration. This is in contrast to evidence documenting aggravation of hyperoxic lung injury following GSH depletion [43]. These data are not contradictory, but serve to illustrate the differences in the pathophysiology of the two forms of lung injury. Acute lung injury in the form of the adult respiratory distress syndrome is PMN mediated and requires a series of sequential events leading to cell activation, upregulation of vascular adhesion molecules, PMN activation, margination, and extravasation—all phenomena which may be attenuated by thiol depletion. Thus, even in the presence of a marked reduction in antioxidant defenses, the failure of PMN influx is of greater significance. By contrast, hyperoxic lung injury occurs through a direct oxidative mechanism, and thus would be aggravated by a reduction in endogenous antioxidant defenses.

These data show that judicious administration of agents which alter the redox state of the cell and hence cellular activation are beneficial in acute inflammatory lung injury. The rapid onset and short duration of thiol depletion associated with DEM treatment, as well as evidence of a posttreatment effect show that it is of therapeutic benefit in limiting lung neutrophil sequestration following both local and remote reperfusion injury, as occurs following lung transplantation or visceral and extremity revascularization, respectively. Further, the ability of DEM to alter leukosequestration in other models [14] suggest a potential for its use in the treatment or prevention of other disease processes characterized by neutrophil-mediated injury.

The compounds of the present invention are thiol depleting agents. In one example, the compounds are DEM, mimetics of DEM, or are compounds containing the active region of DEM or its mimetic responsible for thiol depletion. The compounds may be taken by a number of routes: oral route, rectal route, parenteral route, air passage route, into a body cavity, into the abdominal cavity, by way of examples. They can be used in human therapy as anti-pyretic, anti-inflammatory, mucolitic and analgesic drugs, to prevent reperfusion damages in the post-infarction and reinfarction syndrome and in the ischemic and post-ischemic syndromes. Examples of treatment would be use of the compounds of this invention for patients having had transplants, strokes, myo-cardial infarction, arthritis.

The compounds of this invention are preferably incorporated into pharmaceutical dosage forms suitable for the desired administration route such as tablets, dragees, capsules, granules, suppositories, solutions, suspensions and lyophilized compositions to be diluted to obtain injectable liquids The dosage forms are prepared by conventional techniques and in addition to the compounds of this invention could contain solid or liquid inert diluents and carriers and pharmaceutically useful additives such as liposomes, aggregants, disaggregants, salts for regulating the osmotic pressure, buffers, sweeteners and colouring agents. Slow release pharmaceutical forms for oral use may be prepared according to conventional techniques.

EXAMPLE 1

Effect of Pretreatment with DEM

Figure 2:
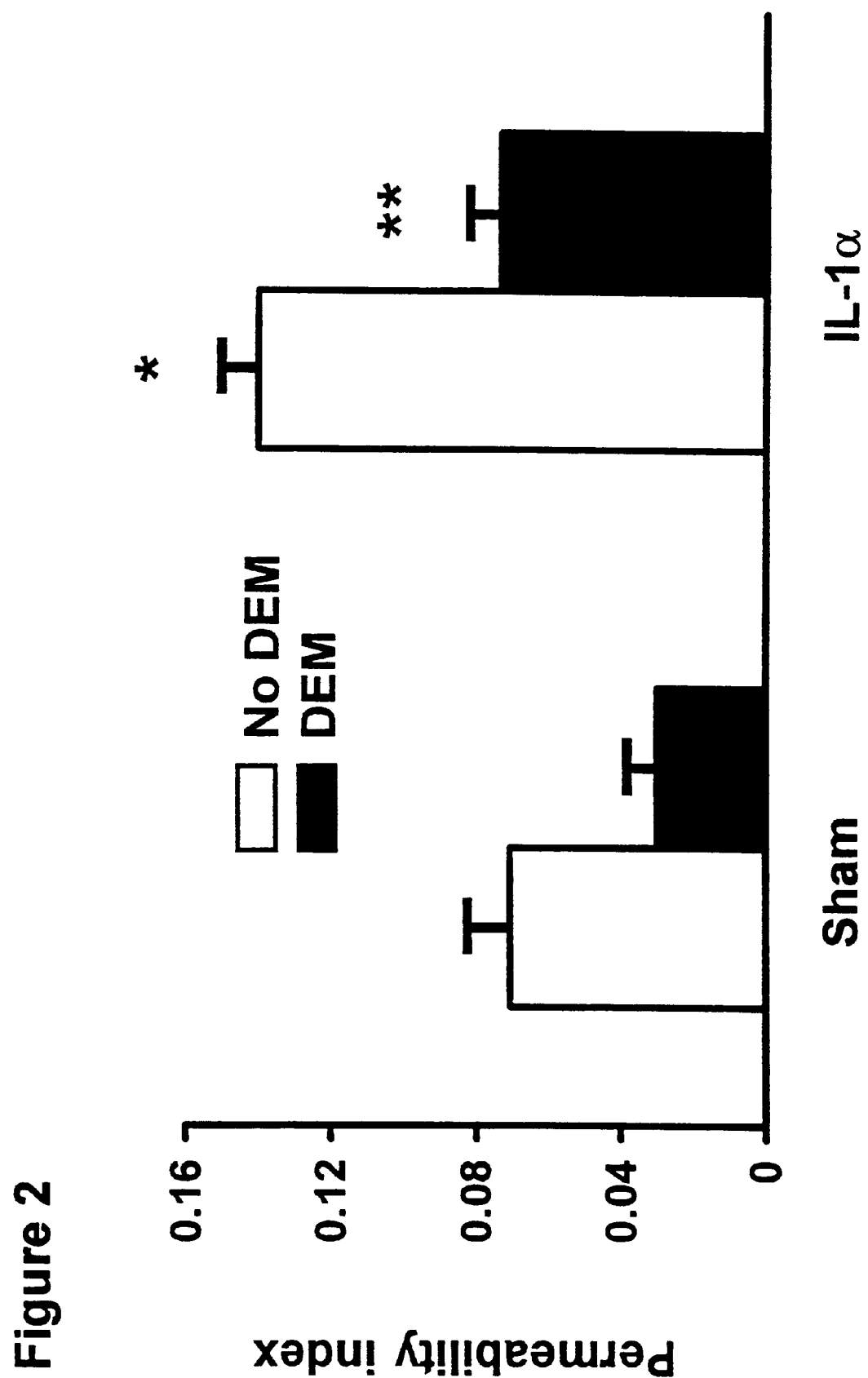
FIG. 2. Animals were pretreated with diethylmaleate (6 mmole/kg) or saline one hour prior to intratracheal IL-1a (50 ng) or vehicle challenge and sacrificed 4 hours later. Lung injury was assessed by pulmonary transcapillary albumin flux as described in methods. Data are expressed as mean±SEM of 4 animals per group. *$p<0.05$ vs sham, **$p<0.05$ vs IL-1a, no diethylmaleate.

Lungs from rats administered intratracheal LPS demonstrated a marked increase in transcapillary albumin flux as compared to sham animals (FIG. 1). By contrast, pretreatment with DEM completely reversed the LPS-induced increase In lung permeability. To determine if DEM exerted its protective effect by means of a paradoxical increase in cellular GSH levels through induction of enzymes critical for de novo GSH synthesis [12], DEM was administered at varying time intervals prior to LPS challenge, and both lung GSH levels and lung permeability were assessed in parallel. Lungs collected from animals receiving DEM 12 hours prior to LPS administration demonstrated a significant increase in lung GSH levels (Table I). Despite increased levels of reduced GSH, there was no evidence of a reduction in lung permeability. However, when DEM was administered closer to the time of LPS administration, there was a significant reduction in lung GSH levels, and with this, a marked reduction in lung permeability. Furthermore, DEM administered concomitant with, or two hours following LPS administration conferred protection. The protective effect of DEM was not specific to LPS, as IL-1a-induced lung injury was similarly attenuated by prior treatment with this agent (FIG. 2).

TABLE 1

Correlation between lung GSH levels and lung permeability index

| Time of DEM injection | LPS | Lung GSH (t = 4 hrs) | Lung PI (t = 4 hrs) |
| --- | --- | --- | --- |
| No DEM | − | 1740 ± 119 | 0.07 ± 0.02 |
| No DEM | + | 1310 ± 114 | 0.22 ± 0.03* |
| −12 | + | 1795 ± 160* | 0.21 ± 0.02 |
| −3 | + | 591 ± 118* | 0.09 ± 0.02† |
| −1 | + | 185 ± 48* | 0.06 ± 0.02† |
| 0 | + | 278 ± 18* | 0.12 ± 0.03† |
| +2 | + | 361 ± 16* | 0.13 ± 0.02† |

Data are mean ± SEM of at least 4 animals per group
*$p < 0.05$ vs no LPS, no DEM; †$p < 0.05$ vs LPS, no DEM

EXAMPLE 2

Reduction in LPS-induced Lung Injury Not Entirely Caused By Respiratory Burst

Figure 3:
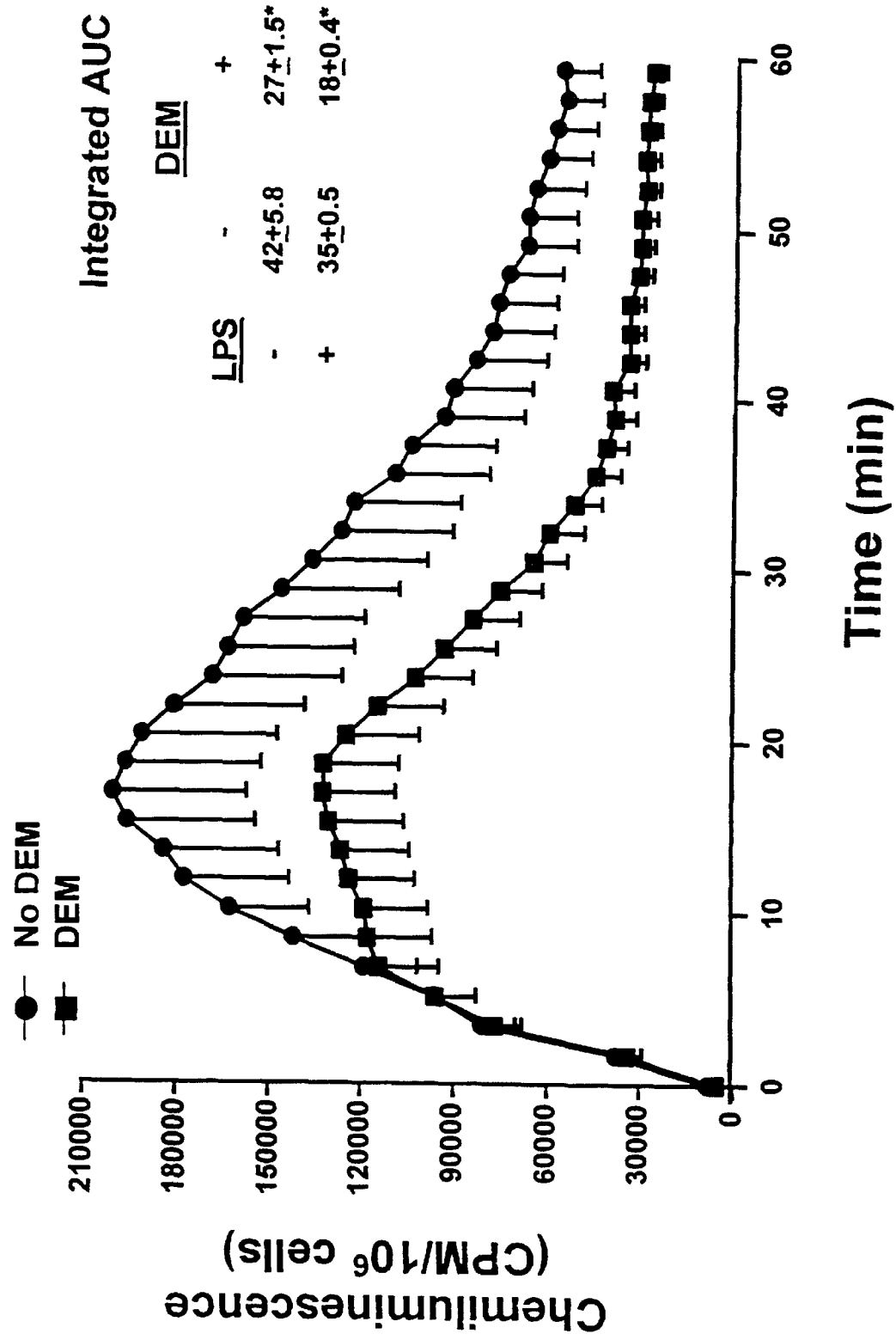
FIG. 3. Peripheral blood neutrophil chemiluminescence as determined by phorbol ester stimulation of whole blood in the presence of the chemiluminigenic probe, luminol. Blood was collected from rats pretreated with diethylmaleate (6 mmole/kg) or saline one hour prior to intratracheal endotoxin (500 mg) and sacrificed 4 hours later. Chemiluminescence was measured every 60 seconds for a period of 60 minutes following addition of phorbol myristate acetate (12.5 $\mu$M). The inset demonstrates the area under the curve (AUC) standardized by the peripheral neutrophil counts in both sham and LPS-treated animals. Data are expressed as mean±SEM of at least 3 animals per group. *$p<0.05$ vs no DEM.

Injury to the pulmonary capillary endothelium occurs in part as a direct consequence of PMN-mediated oxidant injury. To determine whether the reduction in LPS-induced lung injury occurred as a result of impaired PMN oxidant release, the PMN respiratory burst was assessed by evaluating phorbol ester-stimulated whole blood chemiluminescence in animals pretreated with DEM. Following addition of PMA, there is a marked increase in chemiluminescence in saline-treated animals that is only moderately attenuated in animals pretreated with DEM (FIG. 3). These data suggest that reduced generation of a respiratory burst might be contributory, but not entirely responsible for the protective effect.

EXAMPLE 3
Effect of DEM on Lung Neutrophil Sequestration

Figure 4A:
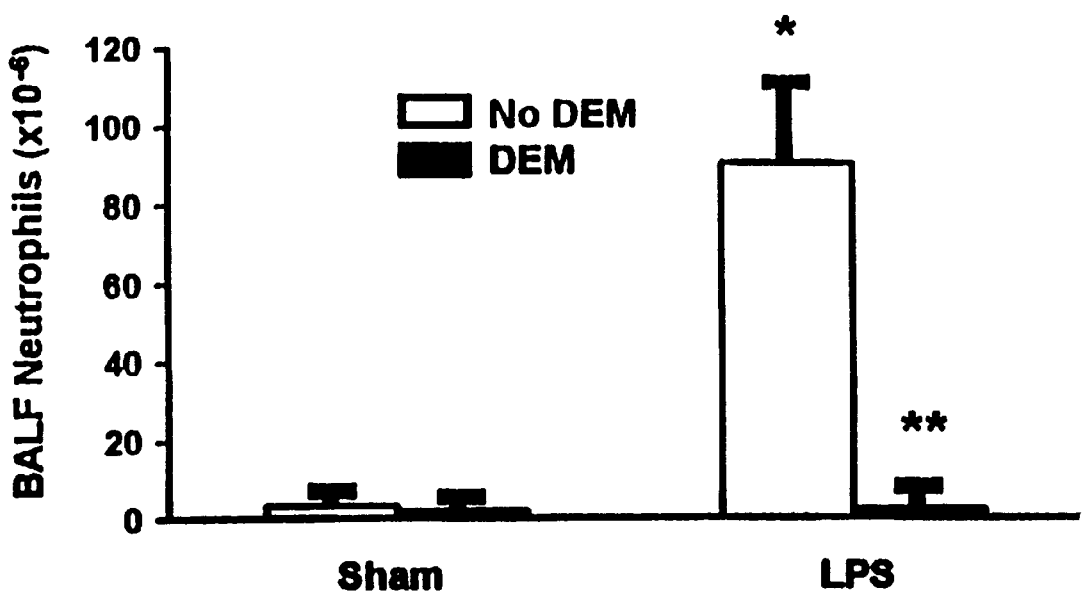
FIG. 4a. Quantitation of bronchoalveolar lavage neutrophils derived from rats pretreated with diethylmaleate (6 mmole/kg) or saline one hour prior to intratracheal endotoxin (500 mg) or vehicle challenge and sacrificed 4 hours later. Data are expressed as mean±SEM of 3 animals per group. *$p<0.01$ vs sham, **$p<0.01$ vs endotoxin, no diethylmaleate.
Figure 4B:
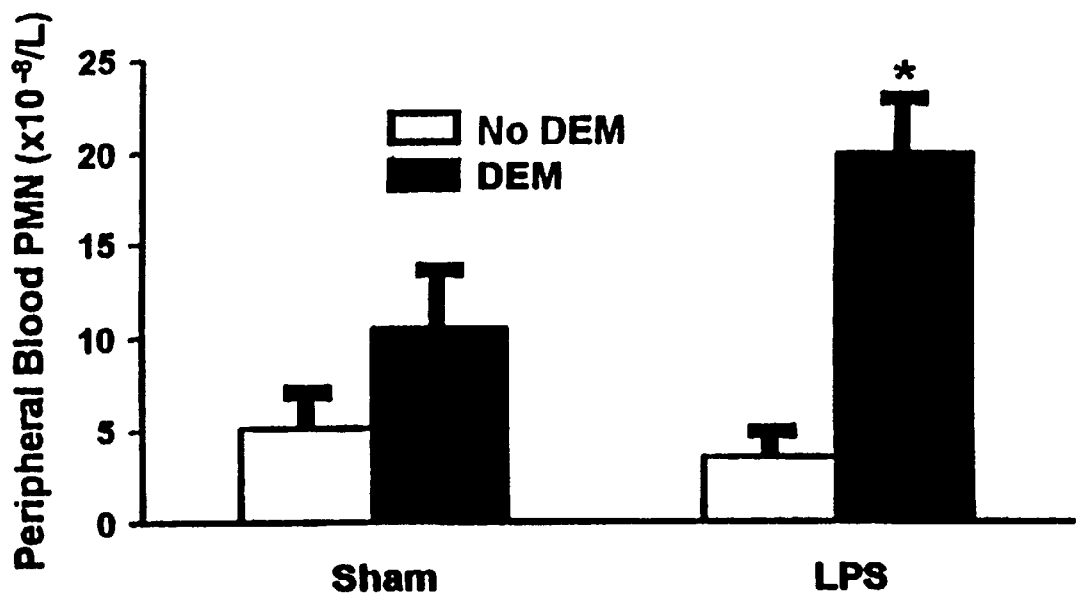
FIG. 4b. Peripheral blood neutrophil counts obtained from rats pretreated with diethylmaleate (6 mmole/kg) or saline one hour prior to intratracheal endotoxin (500 mg) or vehicle challenge and sacrificed 4 hours later. Data are expressed as mean±SEM of 3 animals per group. *$p<0.01$ vs endotoxin, no diethylmaleate.
Figure 5:
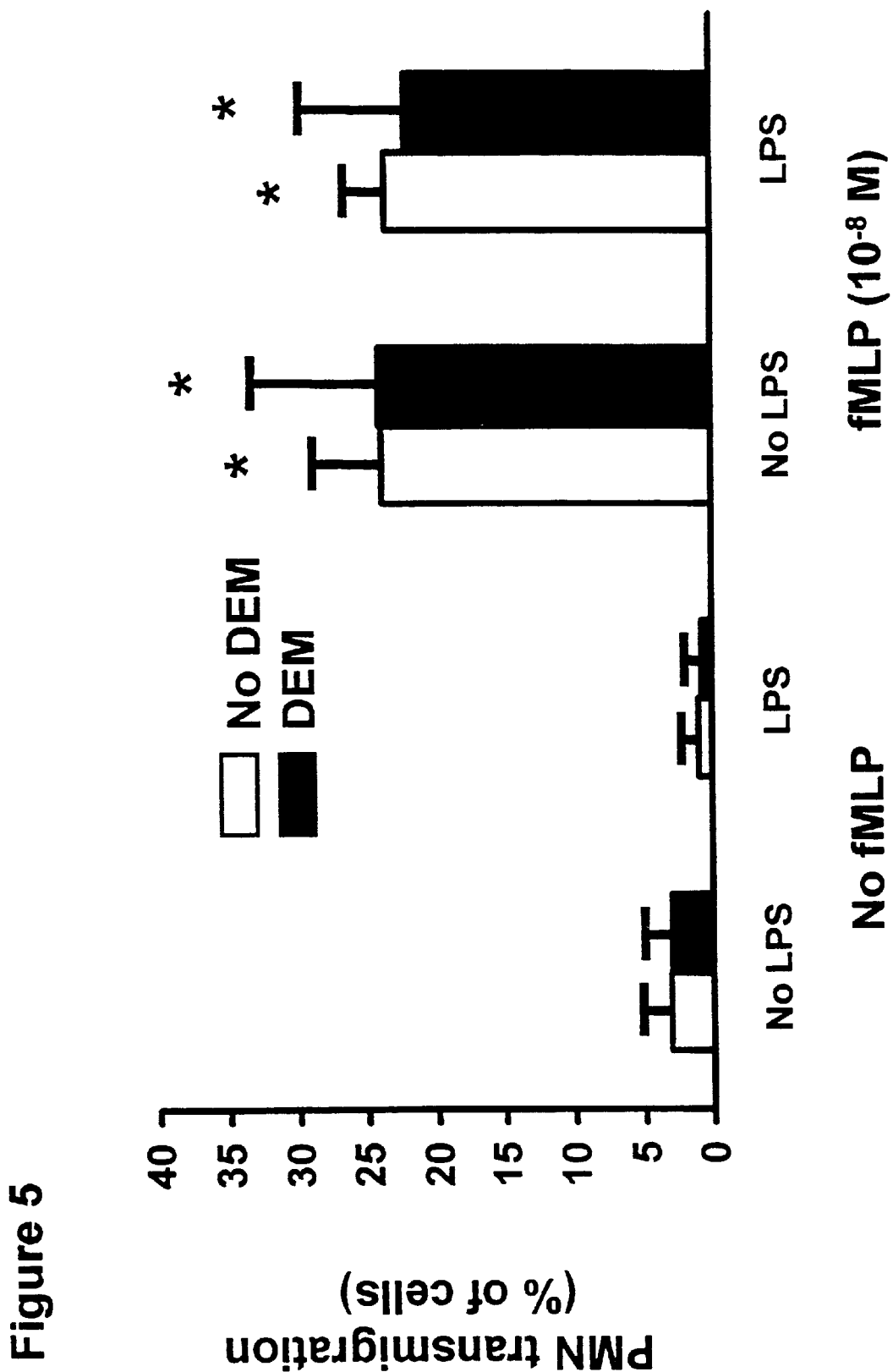
FIG. 5. Neutrophil transmigration across a 3 mM pore polycarbonate filter In response to the chemotactic peptide n-formyl-methionyl-leucyl-phenylalanine (fMLP, $10^{-8}$ M). Peripheral blood neutrophils were isolated from rats pretreated with diethylmaleate (6 mmole/kg) or saline one hour prior to intratracheal endotoxin (500 mg) or vehicle challenge and sacrificed 4 hours later. Data are expressed as mean±SEM of at least 4 animals per group. *$p<0.01$ vs no fMLP.

Lung PMN sequestration and subsequent emigration of cells into the extravascular space are prerequisites for PMN-mediated injury. To determine whether DEM had an effect on lung neutrophil sequestration, BALF was collected and assessed for PMN accumulation. There was a significant increase in BALF neutrophils in LPS-treated animals (FIG. 4a). By contrast, DEM pretreatment completely prevented the increase in BALF neutrophil accumulation. This was not due to depletion of peripheral blood neutrophils, as circulating PMN counts were higher in DEM pretreated animals (FIG. 4b). Further, in vitro studies suggested that neutrophil migration in response to chemotactic stimuli was intact, as peripheral blood neutrophils isolated from control and DEM treated animals demonstrated similar rates of transmigration across a 3 mm pore polycarbonate filter in response to fMLP ($10^{-8}$M) (FIG. 5).

EXAMPLE 4
PMN CD11b Expression Unaffected by DEM Pretreatment

Figure 6:
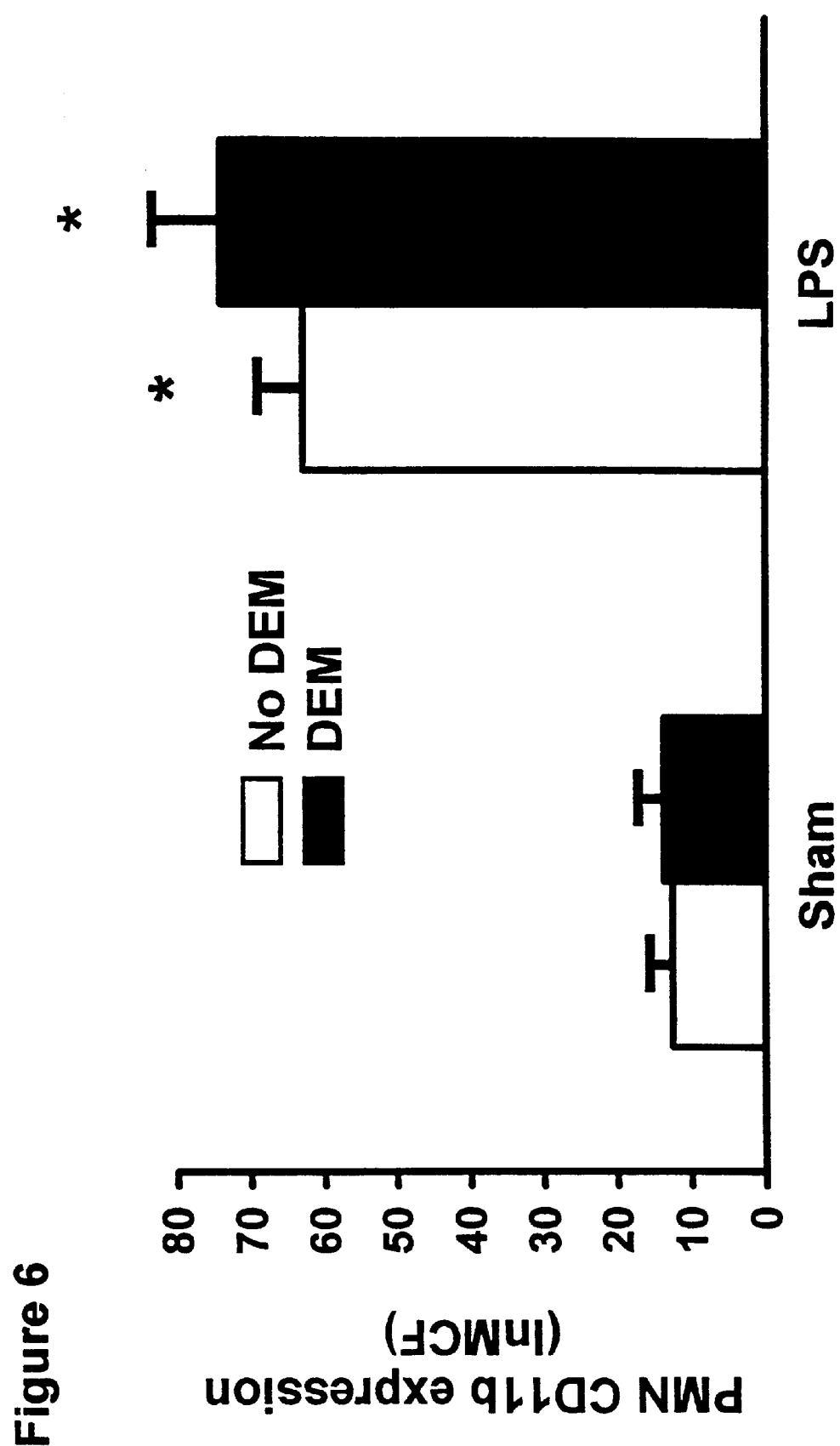
FIG. 6. Expression of CD11b on peripheral blood neutrophils derived from rats pretreated with diethylmaleate (6 mmole/kg) or saline one hour prior to intratracheal endotoxin (500 mg) or vehicle challenge and sacrificed 4 hours later. Peripheral blood neutrophils were stained with FITC conjugated anti-CD11 b mouse anti-rat mAb and analyzed by flow cytometry. Data are mean±SEM of six animals per group. InMCF-log mean channel fluorescence. *$p<0.001$ vs sham.

Lung leukosequestration is dependent on interactions between adhesion molecules expressed on both the PMN and pulmonary capillary endothelium. Alterations in the accumulation of lavage neutrophils may be due to impaired regulation of PMN CD11b/CD18, a $b_2$ integrin previously demonstrated to play an important role in lung PMN sequestration [25]. To determine whether DEM attenuated PMN upregulation of CD11b expression, peripheral blood neutrophijs were obtained from DEM-pretreated animals, and CD11b expression evaluated by flow cytometry using a FITC conjugated anti-CD11b mouse anti-rat mAb. As demonstrated in FIG. 6, PMN CD11b expression in sham animals was unaffected by DEM pretreatment, as LPS administration augmented CD11b/CD18 expression equally in DEM and control animals.

EXAMPLE 5
Pretreatment with DEM Attenuates Endotoxin Induced Upregulation of ICAM-1

Figure 7:
FIG. 7. ICAM-1 expression in lungs from rats pretreated with diethylmaleate (6 mmole/kg) or saline one hour prior to intratracheal endotoxin (500 $\mu$g) or vehicle challenge and sacrificed 4 hours later. Lungs were fixed by intratracheal instillation of methanol/acetic acid and stained with an anti-ICAM-1 mouse ant-rat mAb as described in methods. Magnification-450×. A) No endotoxin, no diethylmaleate; B) endotoxin, no diethylmaleate; C) endotoxin, diethylmaleate.
Figure 7:
Figure 7:
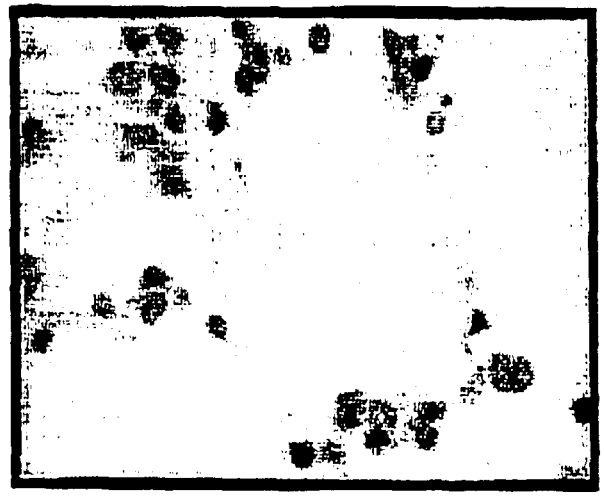
Figure 8:
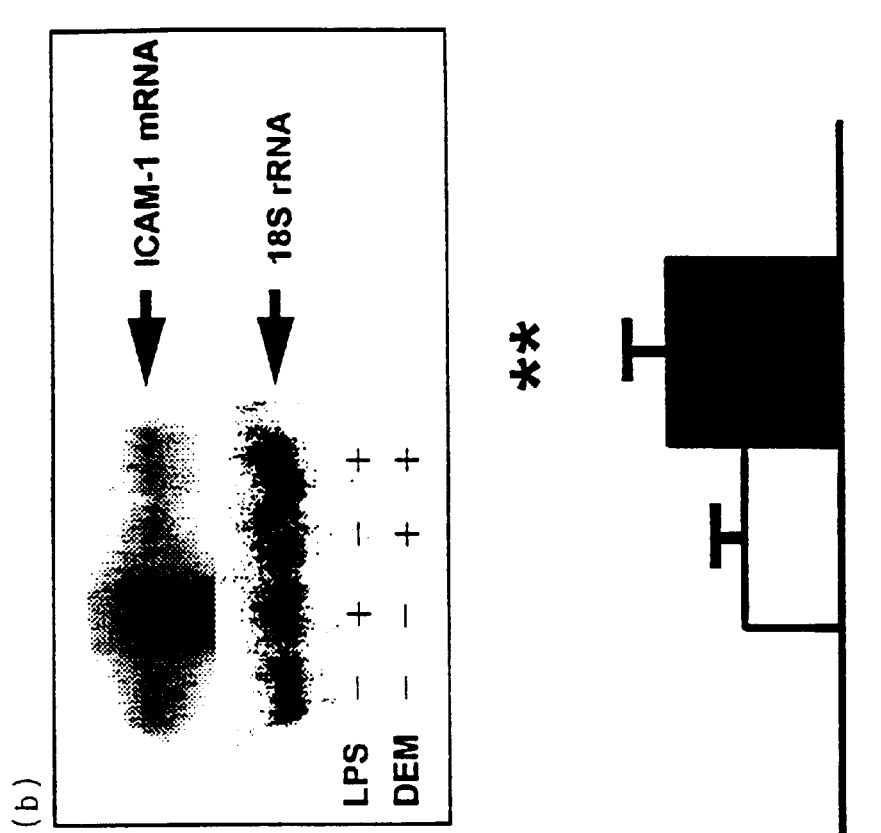
FIG. 8. Northern analysis of ICAM-1 mRNA expression in lungs from rats pretreated with diethylmaleate (6 mmole/kg) or saline one hour prior to intratracheal endotoxin (500 $\mu$g) or vehicle challenge and sacrificed 4 hours later. ICAM-1 mRNA expression was quantitated and normalized to 18S rRNA as described in methods. Data are means SEM of three animals per group. *$p<0.05$ vs sham, **$p<0.05$ vs endotoxin, no diethylmaleate. Inset-representative Northern blot.
Figure 8:

Having demonstrated that neutrophil upregulation of CD11b/CD18 is intact, we assessed whether pretreatment with diethylmaleate attenuated endotoxin induced upregulation of its complementary endothelial ligand, ICAM-1. Immunohistochemical analysis of lungs obtained from sham animals demonstrated low level ICAM-1 expression (FIG. 7). There is a marked increase in staining following treatment with endotoxin. By contrast, upregulation of ICAM-1 expression was completely abrogated in LPS-challenged animals pretreated with DEM. To determine the mechanism for this effect, Northern analysis of lung ICAM-1 mRNA was performed. Constitutive ICAM-1 mRNA expression was detectable in whole lungs obtained from sham animals and was moderately attenuated following DEM pretreatment (FIG. 8). In animals receiving LPS there was almost a four fold increase in ICAM-1 mRNA expression. However, DEM pretreatment almost completely mitigated ICAM-1 upregulation In response to LPS.

Figure 9:
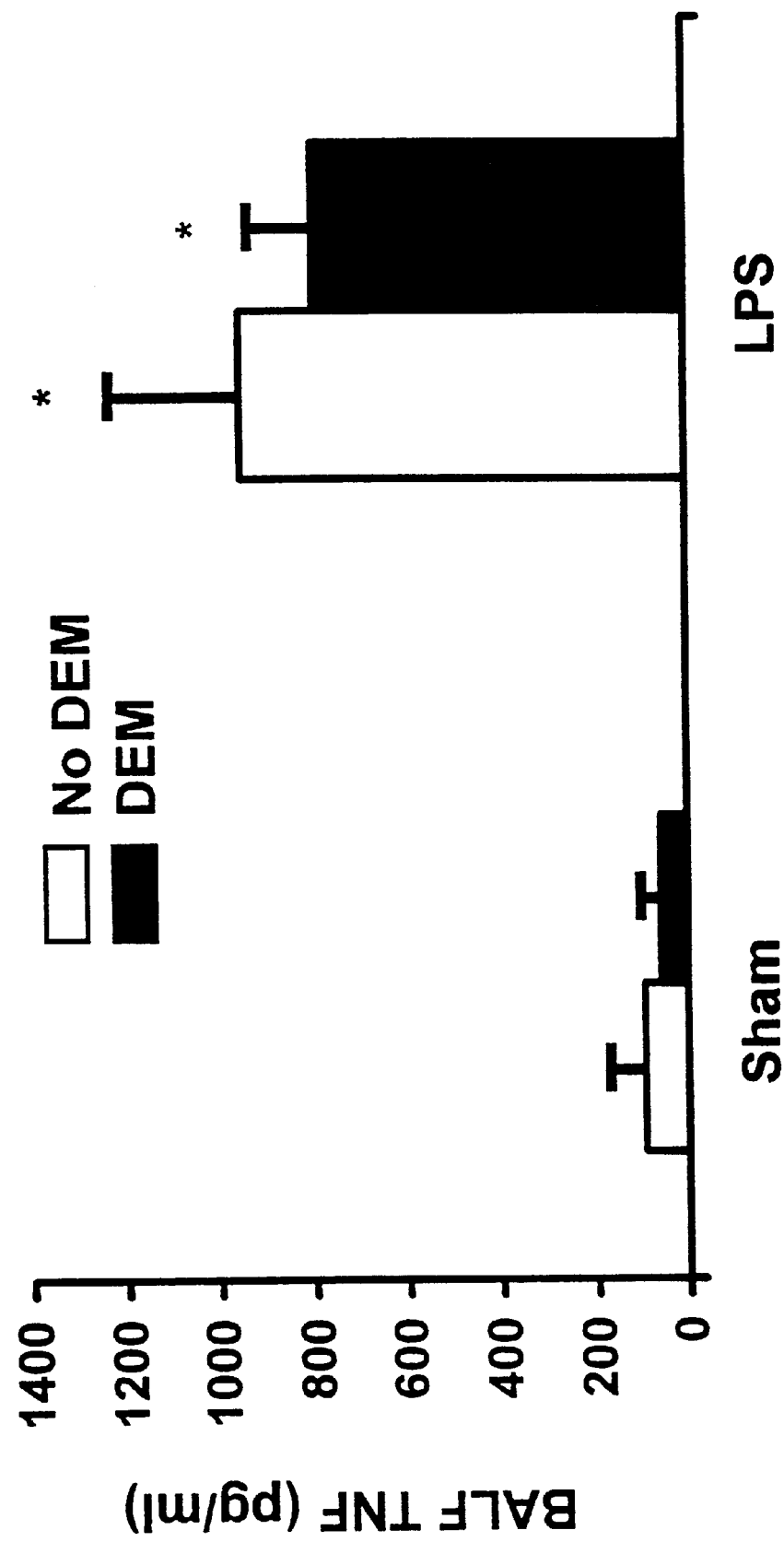
FIG. 9. Bronchoalveolar lavage fluid TNF-a levels in rats pretreated with diethylmaleate (6 mmole/kg) or saline one hour prior to intratracheal endotoxin (500 mg) or vehicle challenge and sacrificed 4 hours later. TNF-a was measured by ELISA. Data are expressed as mean±SEM of at least 4 animals per group. *$p<0.05$ vs sham.

One further possibility is that the cytokine cascade responsible for initiating the local inflammatory response might be attenuated. As an early proinflammatory mediator, TNF-a has been implicated in lung neutrophil sequestration through activation of the pulmonary capillary endothelium and subsequent upregulation of ICAM-1 [26]. Measurement of TNF-a levels in BALF of LPS-treated animals revealed no differences between control and DEM-treated animals, suggesting that initiation of the pulmonary inflammatory response was unaffected (FIG. 9).

EXAMPLE 6
Reduction in ICAM-1 Expression a Direct Effect of DEM

Figure 10A:
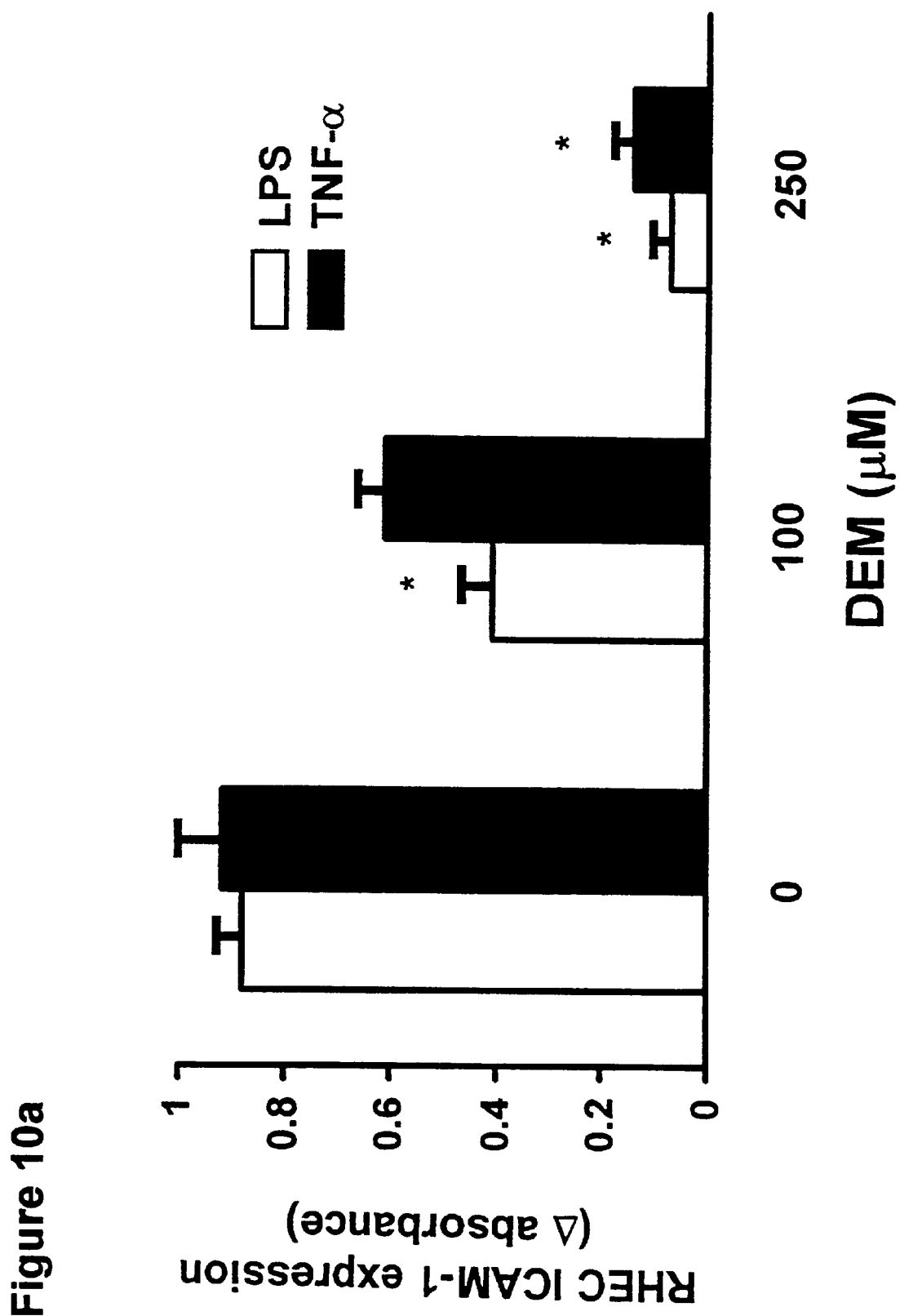
FIG. 10a. Expression of ICAM-1 on endothelial cells pretreated with diethylmaleate (0–250 $\mu$M) 30 minutes prior to addition of either endotoxin (1 mg/ml) or TNF-a (100 ng/ml) for 6 hours. ICAM-1 expression was determined by ELISA as described in methods. Data are mean±SEM of duplicate wells from 4 experiments. *$p<0.01$ vs no diethylmaleate.
Figure 10B:
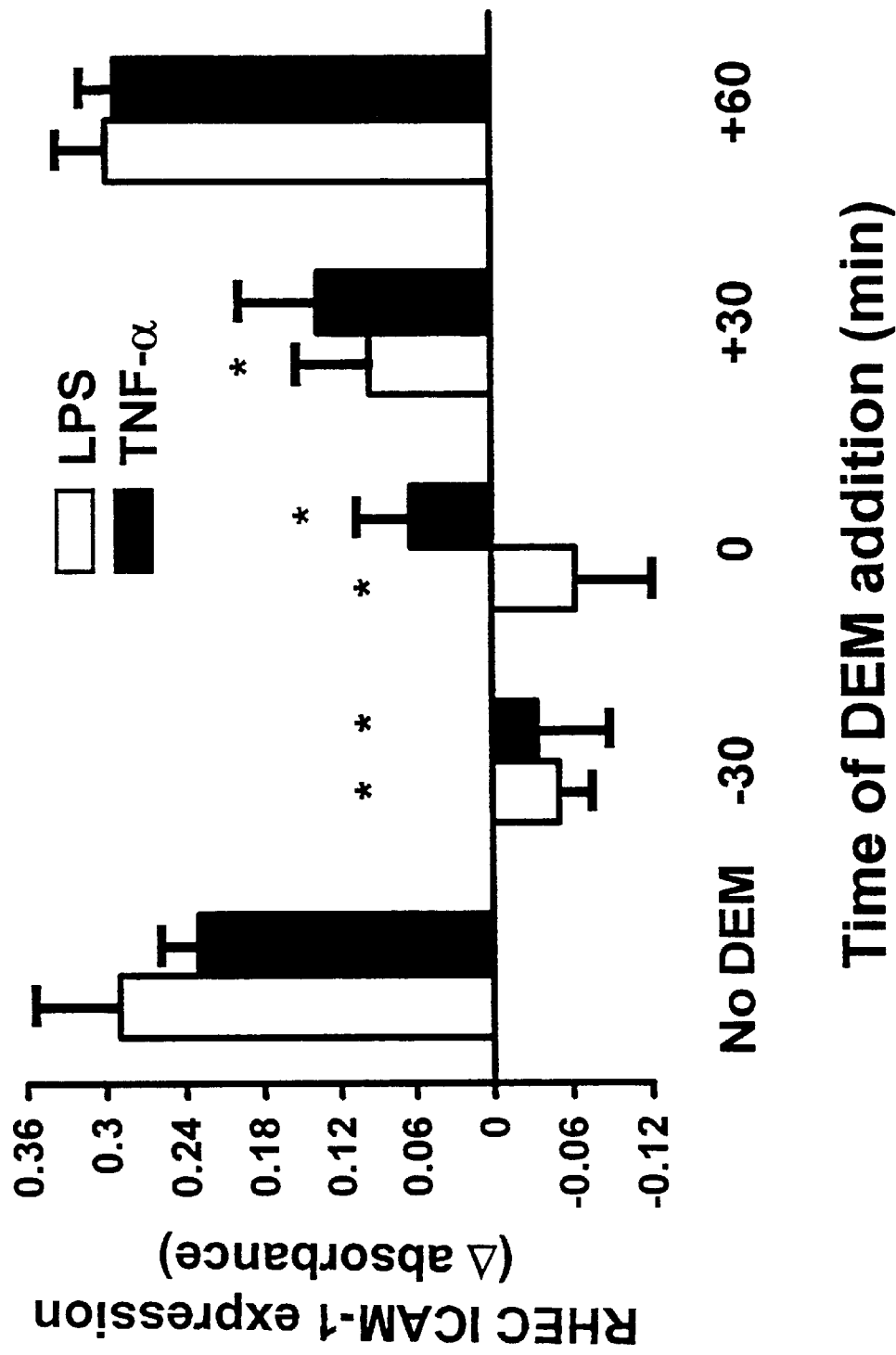
FIG. 10b. Expression of ICAM-1 on endothelial cells following activation with either endotoxin (1 mg/ml) or TNF-a (100 ng/ml) for 6 hours Diethylmaleate (250 $\mu$M) was added from 30 minutes prior (−30) to 60 minutes following (+60) addition of endotoxin or TNF-a. Data are mean±SEM of duplicate wells from 3 experiments. *$p<0.05$ vs no diethylmaleate.

To determine whether the reduction in ICAM-1 expression was a direct effect of DEM, we attempted to recapitulate the effect in vitro using rat heart endothelial cells (RHEC) activated by either LPS or TNF-a. As demonstrated in FIG. 10, DEM prevented the upregulation of ICAM-1 in a dose-dependent fashion. In some experiments, DEM reduced ICAM-1 expression to below constitutive levels. Further, this effect persisted even when DEM was added 30 minutes following cell activation. Additionally, DEM did not impair ICAM-1 binding by the primary antibody, as normal levels of ICAM-1 expression were detected with delayed addition (in excess of 60 minutes) of DEM. Diethylmaleate did not affect cell viability as determined by trypan blue exclusion, nor the integrity of the cell monolayer. Moreover, supernatant lactate dehydrogenase levels were unaffected, demonstrating that diethylmaleate was not cytotoxic to the RHEC (Table II).

TABLE II

Cytotoxicity of diethylmaleate: supernatant lactate dehydrogenase activity (U/L)

| RHEC treatment | No DEM | DEM |
| --- | --- | --- |
| Control | 43.5 ± 3.5 | 32.5 ± 3.5 |
| LPS (1 mg/ml) | 38.0 ± 1.0 | 33.0 ± 4.0 |
| TNF-a (100 ng/ml) | 40.5 ± 2.5 | 33.5 ± 2.5 |

Data are mean ± SEM of replicate wells from 2 separate experiments.

EXAMPLE 7
DEM Prevents Early Inflammation in Antigen-Induced Arthritis (AIA)

Alterations in the cellular redox state play a critical role in cell activation, suggesting an important role for sulfhydryl-reactive agents in modulating the inflammatory response. We examined the effect of intracellular thiol depletion in antigen-induced arthritis (AIA) with the administration of diethylmaleate (DEM) which is known to deplete glutathione. AIA was induced by sensitizing Lewis rats with 2 subcutaneous injections of methylated bovine serum albumin (1 mg/ml), then administering an intra-articular injection of mBSA. This protocol induced an intense inflammatory cell infiltration of neutrophils, macrophages and lymphocytes as early as 4 hours following intra-articular injection In animals given a single ip injection of DEM (6 mmole/kg) 1 hour prior to antigen there was almost complete attenuation of the inflammation seen (quantitative histopathology scores 0 with DEM vs 3+ without DEM pre-treatment). At 48 hours the single DEM effect had resolved with treated and untreated animals showing comparable severity of arthritis.

Acute inflammation in AIA is dramatically attenuated by DEM-induced glutathione depletion. We have previously demonstrated that DEM abrogates upregulation of ICAM-1 by endothelial cells. This implicates intracellular thiols and consequently endothelial cell adhesion molecules as being central in mediating acute synovitis.

EXAMPLE 8
Effect of the Thiol Oxidizing Agent Diethylmaleate on Endothelial Cell (EC) Activation The redox state of the cell has been shown to modulate several aspects of cell function including gene activation, protein traffick, and protein function. We have previously demonstrated that diethylmaleate (DEM), a thiol oxidizing agent is able to attenuate lung injury in a rat model. These studies showed that neutrophil (PMN) influx into the lung was totally prevented when DEM was administered at the time of the inflammatory stimulus LPS. This suggested that impaired PMN sequestration might be responsible for the protective effect. Subsequent studies demonstrated that while PMN adhesion molecules were normally upregulated in vivo in the presence of DEM, this agent completely prevented expression of the EC adhesion molecule ICAM-1 in response to LPS. This was demonstrated by immunohistochemistry of lungs as well as Western blot analysis. Further, DEM totally prevented the increase in levels of ICAM-1 mRNA following LPS treatment In vitro studies using human umbilical vein endothelial cells (HUVEC) mimicked this effect by showing that DEM prevented upregulation of ICAM-1 protein and gene expression. These observations suggest a novel antiinflammatory effect of thiol oxidizing agents.

To evaluate the mechanism whereby DEM exerts its effect and to further evaluate the potential for this agent in related inflammatory disease processes, studies are performed both in vitro and in vivo. In vitro studies use the HUVEC to study the mechanism of DEM's effect on level of ICAM-1. Reduced levels of ICAM-1 transcripts may be due to reduced transcription rate or altered mRNA stability. The latter are studied by stability assays monitoring the rate of decay of the transcripts following administration of actinomycin D. The former are evaluated by transcription assays. To define whether the effect of DEM on EC is global, we evaluate other EC adhesion molecules including VCAM, E-selectin and PECAM as well as other functional molecules known to be upregulated during inflammation, such as the procoagulant tissue factor. In vivo studies focus on whether the effect of DEM on inflammation can be generalized. Two other models where PMN influx is important to pathophysiology are studied. One is an acute arthritis model using intraarticular albumin and the other is an ischemia-reperfusion model of liver injury, a process is important to transplantation. Injury, PMN influx, and adhesion molecule expression will be used as endpoints in these studies.

EXAMPLE 9

The Effect of DEM in the Prevention of Local and Distant Injury Following Ischemia-Reperfusion of the Gastrointestinal Tract Advances in prehospital care and early management of severely injured critically ill patients has resulted in a significant reduction in early deaths due to trauma. However, late deaths in patients suffering major injuries are not uncommon, with the most frequent etiology being acute respiratory failure as a result of the acute respiratory distress syndrome (ARDS). ARDS develops in excess of 25% of patients with significant multisystem injuries and has a mortality in the range of 40% (1).

ARDS is a form of acute lung injury mediated to a large extent by the neutrophil (2,3). The critical importance of the neutrophil in mediating injury suggests that strategies aimed at limiting lung neutrophil influx may offer the greatest clinical benefit in preventing lung injury. The sequestration of neutrophils into inflammatory sites is dependent on interactions between cell surface molecules expressed on the neutrophil and their endothelial counter-ligands, the most important of which are the $b_2$ integrins and intercellular adhesion molecule-1 (ICAM-1), respectively (4,5).

Cell activation is necessary for upregulation of both neutrophil and endothelial adhesion molecules. Alterations in the intracellular redox state can have profound effects on cell activation (6–8). We have demonstrated that the glutathione depleting agent, diethylmaleate (DEM), prevents neutrophil sequestration in the lung in response to a variety of inflammatory stimuli. The mechanisms accounting for these effects have yet to be elucidated. Neutrophil function as evidenced by respiratory burst, upregulation of adhesion molecules and ability to migrate was shown to be normal. Altered ICAM-1 expression in DEM-treated animals might be responsible for the impairment of neutrophil sequestration. DEM-treated animals exposed to intratracheal LPS exhibited no upregulation of ICAM-1 compared to LPS alone. Further, while LPS increased the levels of ICAM-1 gene expression, this was totally prevented by DEM. Considered together, these data suggest that DEM alters ICAM-1 expression at the level of the gene. Importantly, these findings suggest a novel therapeutic approach to the management of pathophysiological process which result from neutrophil influx into tissues and subsequent oxidant-mediated injury. As a general group, processes involving ischemia-reperfusion, as might occur during major resuscitation following trauma or infection, fall into this category.

The purpose of the present studies is to evaluate the mechanism by which glutathione depletion exerts its effects on ICAM-1 expression and to show that this agent is effective at preventing lung injury in an animal model relevant to the development of ARDS in the posttrauma period. We showed that the effect of DEM on ICAM-1 expression mitigates lung neutrophil influx and thus prevent lung injury.

The mechanism by which neutrophils and the pulmonary capillary endothelium are activated to allow for lung neutrophil sequestration in trauma patients is unclear. One putative mechanism is that during periods of hypotension, there is a relative degree of splanchnic ischemia (9). Following resuscitation, the small bowel and liver undergo a reperfusion injury. Neutrophils are then primed as they pass through the mesenteric vascular bed (10). Within 60 minutes of reperfusion, there is an increase in circulating pro-inflammatory mediators which serve to activate the pulmonary capillary endothelium, leading to upregulation of vascular adhesion molecules, and subsequently, lung neutrophil sequestration (11). Pulmonary capillary ICAM-1 expression is necessary for the development of lung sequestration, as administration of antibodies directed against ICAM-1 in animals undergoing gut ischemia-reperfusion prevents lung neutrophil influx (12). These data show that diethylmaleate is effective in preventing lung neutrophil sequestration and subsequent injury.

This rodent model of gut ischemia-reperfusion has previously been described (11). Animals are randomly assigned to one of four groups: Sham operation or gut ischemia-reperfusion with or without DEM treatment. For the gut ischemia-reperfusion, male Sprague Dawley rats (250 gm) are anesthetized with pentobarbital (50 mg/kg). Via a midline laparotomy, collateral vessels from the celiac axis are ligated and the superior mesenteric artery occluded with a microvascular clamp. After one hour, the clamp is removed and mesenteric reperfusion documented by the return of normal color to the bowel wall. The laparotomy incision is then closed and animals sacrificed by exsanguination at varying time intervals (up to 6 hours) following reperfusion. Shams are similarly treated but without SMA occlusion. DEM or saline vehicle are administered by intraperitoneal injection (1 cc/kg) at times ranging from 1 hour prior to the induction of ischemia to 3 hours following is reperfusion.

Lung injury is assessed by determining the transpulmonary flux of $^{125}$I-albumin. Thirty minutes prior to sacrifice, animals receive an intravenous injection of $^{125}$I-albumin (1 mCi). At the time of sacrifice, the lungs are rendered blood free by perfusing the pulmonary artery with a low-potassium-dextran solution. Lung and a sample of blood are collected for measurement of the ratio of lung:blood radiolabel. This ratio is a sensitive measure of lung injury and correlates well with histologic indices of tissue damage.

To determine the mechanism by which this agent reduces lung injury, lung neutrophil sequestration are evaluated by measuring lung myeloperoxidase (MPO) activity. MPO represents 95% of the dry weight of the neutrophil and thus is an excellent marker of neutrophil content. Histologic confirmation of alterations in neutrophil influx serve as an independent means of assessing the effect of DEM.

If DEM prevents lung neutrophil influx, the mechanism for this effect is evaluated using both cellular and molecular approaches. Lung sections are fixed in acetic acid/methanol and stained with an anti-ICAM-1 antibody using standard immunohistochemical techniques. ICAM-1 mRNA expression is evaluated following total lung RNA extraction and Northern analysis with a specific cDNA probe.

We also evaluate the intestine with respect to the occurrence of ischemia-reperfusion injury locally. Specifically, neutrophil sequestration is studied by histology and MPO, and the integrity of the mucosal barrier is evaluated electrophysiologically using Ussing chamber techniques.

Considered together, these studies determine the mechanisms whereby diethylmaleate is able to protect the GI tract locally and the lungs at a distance from injury related to ischemia-reperfusion of the intestine.

Several events critical to cell activation may be modulated by alterations In intracellular thiol levels. For example, protein kinase activation (13,14), gene activation (15,16), regulation of mRNA stability (17), as well as post-translational processing (18) have all been reported to be regulated by changes in the intracellular redox state, reflected in a decrease in the reduced glutathione (GSH) to glutathione disulfide ration (GSSG). The promoter region of the ICAM-1 gene has al consensus binding sequence for the transcription factor nuclear factor kB (NF-κB) (19). Activation of NF-κB is profoundly redox-sensitive, suggesting that-alterations in GSH/GSSG ratio may alter gene activation (15). The effect of thiols on gene expression is not limited to gene activation. The ICAM-1 mRNA has an AU rich motif in its 3' untranslated region which targets the mRNA for rapid degradation (20). An AU binding factor (AUBF) normally binds to this motif, and prevents early degradation of mRNA (21). A reduction in reduced intracellular thiols may prevent AUBF from binding to this target sequence, resulting in a reduction in mRNA stability (13). Glutathione depletion by DEM prevents ICAM-1 mRNA expression in response to inflammatory stimuli in vivo. The mechanism for this effect remains to be elucidated, but points to either a reduction in the rate of In vitro studies are carried out using human umbilical vein endothelial cells (HUVEC) isolated by standard techniques. Cells are activated with the proinflammatory cytokine tumor necrosis factor-a (TNF-a, 100 ng/ml) for up to 6 hours. ICAM-1 protein and mRNA expression are evaluated by ELISA and Northern analysis, respectively. If the results are consistent with our in vivo studies, we anticipate a dramatic reduction in levels of protein and mRNA expression in cells pretreated with DEM. To determine the mechanism for the reduction in mRNA expression, transcriptional run-on analyses are performed. This allows an assessment of whether DEM is affecting the rate of ICAM-1 mRNA transcription. If a reduction in the rate of transcription is evident, than electrophoretic mobility shift assays (EMSA) using nuclear extracts are necessary to determine the effect of glutathione depletion on activation and binding of NF-κB to its consensus motif in the promoter region of the ICAM-1 gene. If there is no change in the rate of ICAM-1 mRNA transcription, then attention focuses on the effect of DEM on ICAM-1 mRNA stability. This is evaluated by adding actinomycin D to the culture system to induce transcriptional arrest, followed by harvesting of cells at serial intervals for Northern analysis. If a reduction in mRNA stability is documented, then EMSA is performed using extracts of total cellular RNA to determine the effect of glutathione depletion on binding of the AUBF to its recognition sequence in the 3'-untranslated region of ICAM-1 mRNA.

EXAMPLE 10

DEM Attenuated Local Skin Inflammation by a NF-κB Mediated Reduction in ICAM-1

The redox state of the cell has been shown to regulate cell activation. The thioloxidizing agent DEM prevents lipopolysaccharide (LPS)induced upregulation of endothelial cell ICAM-1 in vitro (Surg. Forum 1996). To determine if this process was active in vivo, we explored the effect of DEM in a dermal inflammation model characterized by PMN influx.

Swiss Webster mice were injected intradermally with saline or LPS (30 μg) with or without ip DEM or vehicle. Injection sites were harvested after 24 hours and evaluated for change in vascular permeability, using $I^{125}$-labelled albumin and for levels of ICAM-1 mRNA (Table III).

| Group | PI (mean ± SEM) |
|---|---|
| control | 0.99 ± 0.13 |
| LPS id | 6.00 ± 0.81* |
| LPS + DEM 3 mmol/kg | 4.03 ± 0.43 |
| LPS + DEM 6 mmol/kg | 0.84 ± 0.28** |

*p < 0.01 vs cont;
**p < 0.001 vs LPS;
n = 7–18/grp

Figure 11:
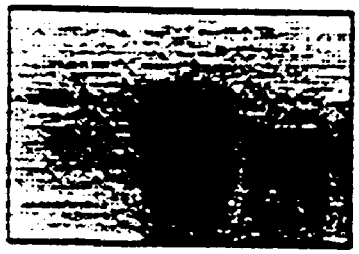
FIG. 11. Effect of DEM on LPS-induced upregulation of ICAM-1 mRNA in skin of mice injected intradermally with LPS (30 $\mu$g). ICAM-1 Northern blot.
Figure 12:
FIG. 12. Effect of DEM on NF-κB binding. Electrophoretic mobility shift assay on human umbilical vein endothelial cells in vitro.

DEM decreased skin permeability index (PI) in a dose dependent fashion; DEM alone had no effect. In keeping with the hypothesized mechanism, DEM (6 mmol/kg) also prevented the LPS-induced upregulation of ICAM-1 mRNA (FIG. 11). ICAM-1 gene expression is regulated by NF-κB binding to its promoter. To determine whether DEM altered NF-κB binding, an electrophoretic mobility shift assay (EMSA) was performed on human umbilical vein endothelial cells In vitro (FIG. 12). DEM abrogated the LPS-dependent increase in NF-κB binding.

These results show that DEM markedly attenuates LPS induced dermal inflammation via an NF-κB mediated reduction in ICAM-1 expression. These data also show that manipulation of the intracellular redox state has a beneficial role in neutrophil-mediated inflammation. Other thiol depleting agents, such as phorone and B.S.O, which decrease ICAM-1 expression without altering the experssion of other proteins (such as TNF) are also beneficial in reducing neutrophil-mediated inflammation.

Examples 11 to 17 demonstrate that DEM and another GSH depleting agent, phorone, prevent the upregulation of endothelial cell ICAM-1 expression in vivo and in so doing, mitigates PMN influx into the lung. In vitro studies demonstrate that this affect is a direct one on the endothelium and is sufficient to prevent PMN migration across an endothelial cell monolayer. Finally, the effect is not specific to the pulmonary capillary bed, since neutrophil migration into the peritoneal cavity following induction of chemical peritonitis is prevented by DEM pretreatment.

Figure 13A:
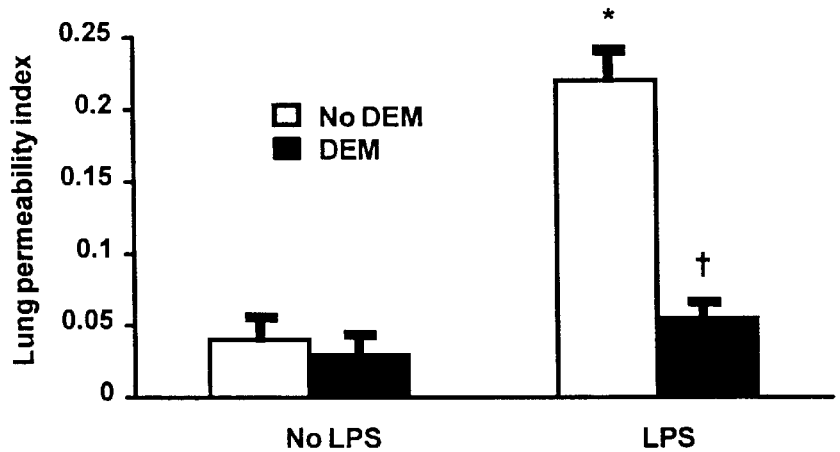
FIG. 13a. Effect of diethylmaleate (DEM) on lung injury as assessed by the transcapillary flux of $^{125}$I-albumin. Animals were pretreated with DEM (6 mmole/kg) or saline by intraperitoneal injection one hour prior to intratracheal endotoxin (500 mg) or vehicle challenge and sacrificed 4 hours later. Data are expressed as mean±SEM of at least 4 animals per group. *$p<0.001$ vs no LPS, †$p<0.001$ vs LPS, no DEM.
Figure 13B:
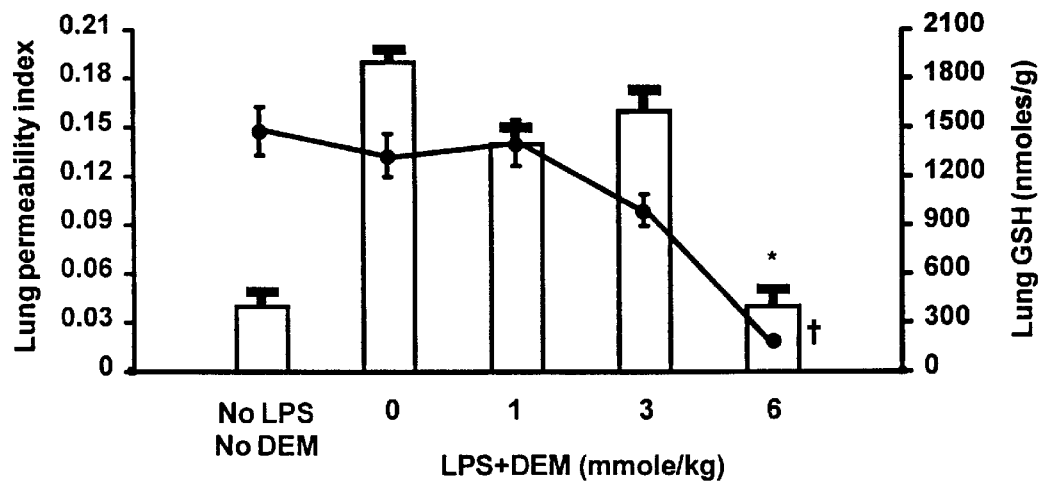
FIG. 13b. Effect of increasing the administered dose of DEM on lung injury and lung thiol levels. Data are expressed as mean±SEM of 4 animals per group. Bars-permeability index, solid line-lung thiol levels. *$p<0.001$ vs LPS, no DEM (0 mmole/kg). †$p<0.001$ vs LPS, no DEM. Data are expressed as mean±SEM of 4 animals per group.
Figure 14A:
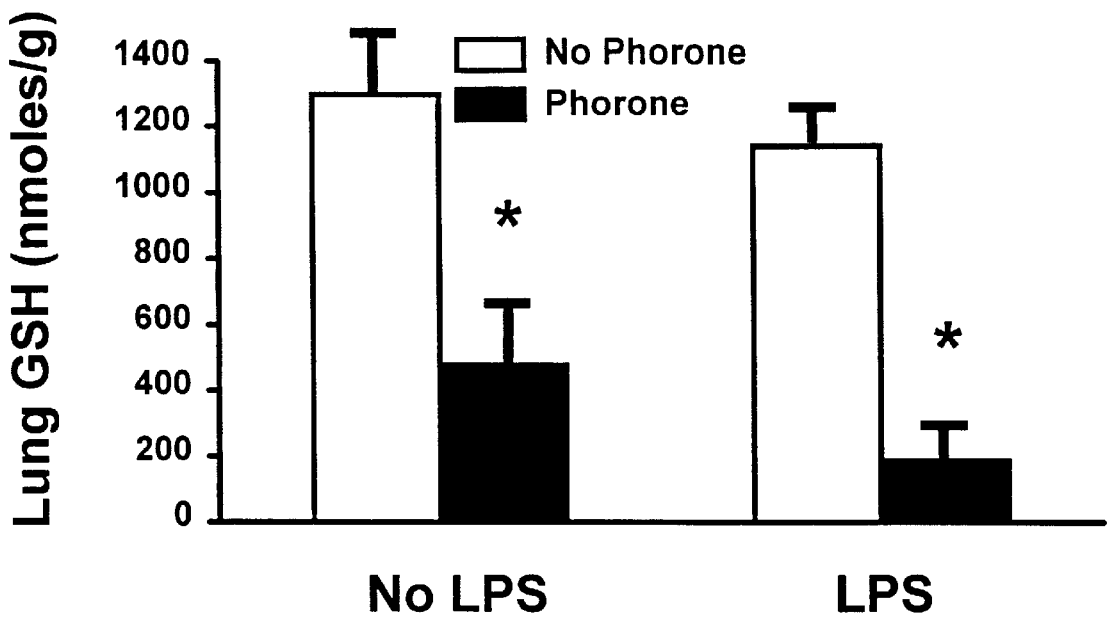
FIG. 14a. Effect of phorone on lung thiol levels. Animals were pretreated with phorone (250 mg/kg) or saline by intraperitoneal injection one hour prior to intratracheal endotoxin (500 mg) or vehicle challenge and sacrificed 4 hours later. Data are expressed as mean±SEM of 4 animals per group. *$p<0.001$ vs no phorone.
Figure 14B:
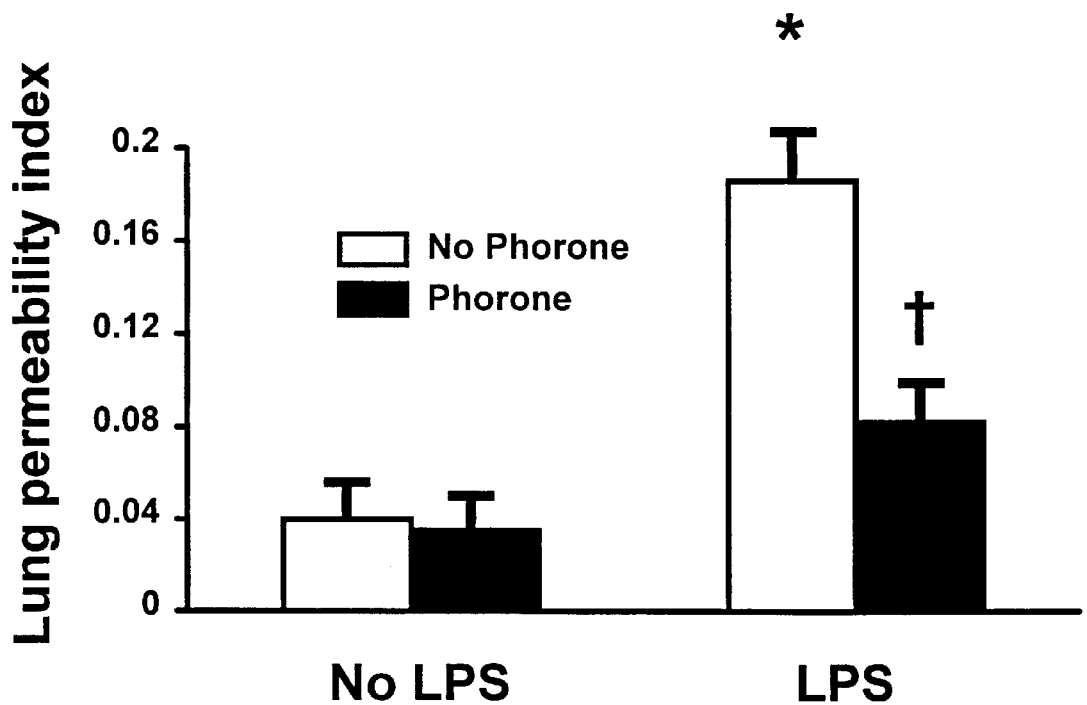
FIG. 14b. Effect of phorone on LPS-induced lung injury. Animals were pretreated with phorone (250 mg/kg) or saline by intraperitoneal injection one hour prior to intratracheal endotoxin (500 mg) or vehicle challenge and sacrificed 4 hours later. Data are expressed as mean±SEM of 4 animals per group. *$p<0.001$ vs no LPS, †$p<0.001$ vs LPS, no phorone.

EXAMPLE 11
Pretreatment with DEM Prevents the Increased Permeability Associated with LPS Challenge by Depletion of Glutathione Intratracheal challenge with LPS caused a significant increase in the lung permeability Index (Control: 0.04±0.02 vs LPS:0.22±0.03; (p<0.001) as assessed by the transcapillary flux of radiolabelled albumin (FIG. 13A). Pretreatment with a single dose of DEM (6 mmole/kg, ip) one hour prior to intratracheal challenge had no effect on lung permeability in control animals, yet completely prevented the increase in permeability associated with LPS challenge. This protective effect was not evident at doses less than 6 mmole/kg (FIG. 13B). Two lines of evidence suggest that the effect of DEM was related to its ability to deplete glutathione. First, DEM conferred protection at 6 mmole/kg but not at lower doses. Only at this dose was there a significant reduction in lung thiol levels as GSH levels were comparable to the control group when treated with lower doses of DEM. Second, we evaluated the effect of phorone, another rapidly acting GSH depleting agent. Phorone (250 mg/kg) administered by intraperitoneal administration 1 hour prior to intratracheal LPS challenge induced a comparable reduction in lung GSH levels comparable to that seen with DEM (FIG. 14A). As shown in FIG. 14B, treatment with phorone recapitulated the effect on lung permeability demonstrated with DEM, with almost complete prevention of the increase in lung permeability induced by LPS challenge.

EXAMPLE 12
Histologic Evaluation of Lung Tissue Following LPS Treatment

Figure 15:
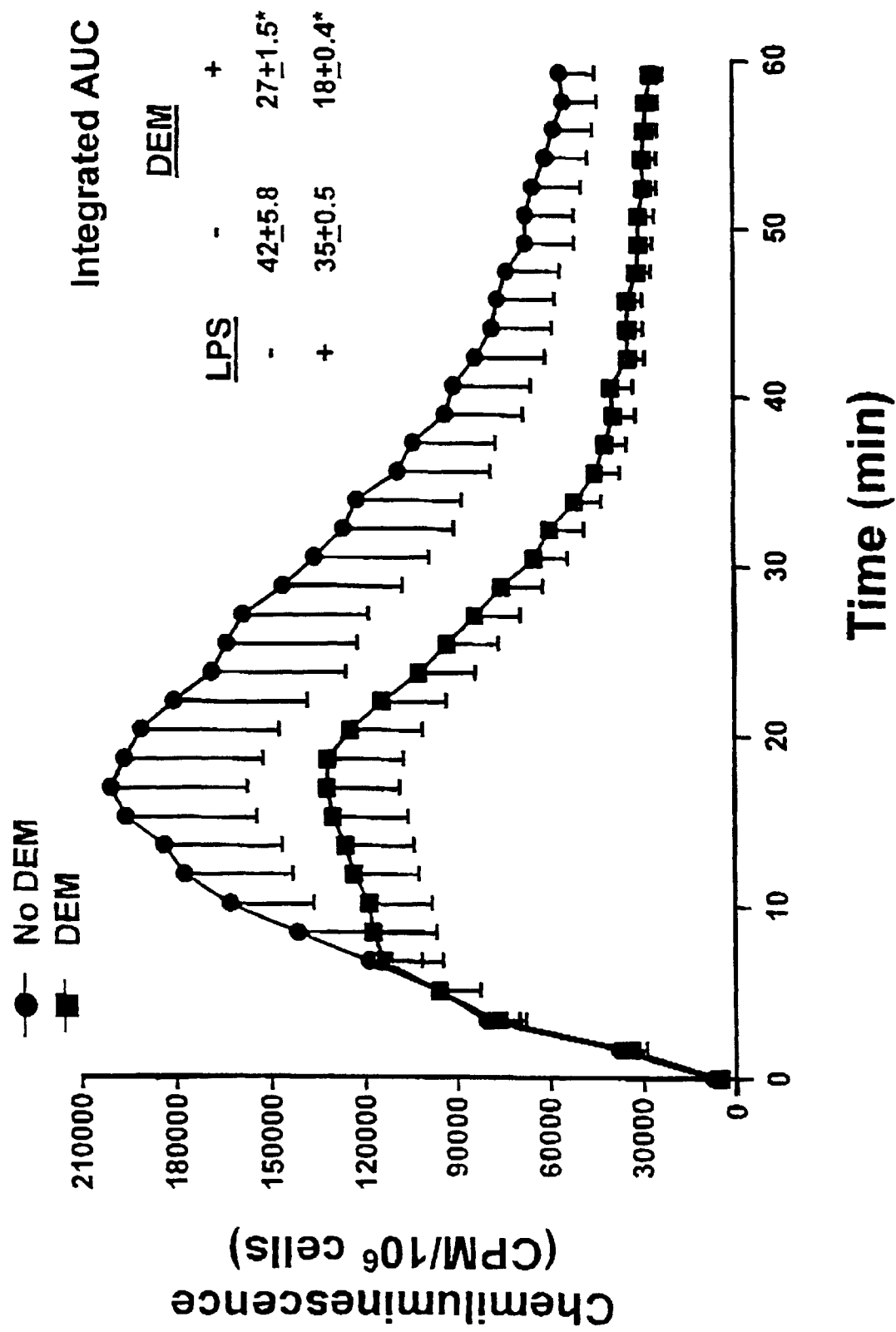
FIG. 15. Histologic evaluation of lungs derived from animals pretreated with DEM. Animals were pretreated with diethylmaleate (DEM, 6 mmole/kg) or saline by intraperitoneal injection one hour prior to intratracheal endotoxin (500 mg) or vehicle challenge and sacrificed 4 hours later. Sections were stained with hematoxylin and eosin. Magnification-300×.
Figure 16:
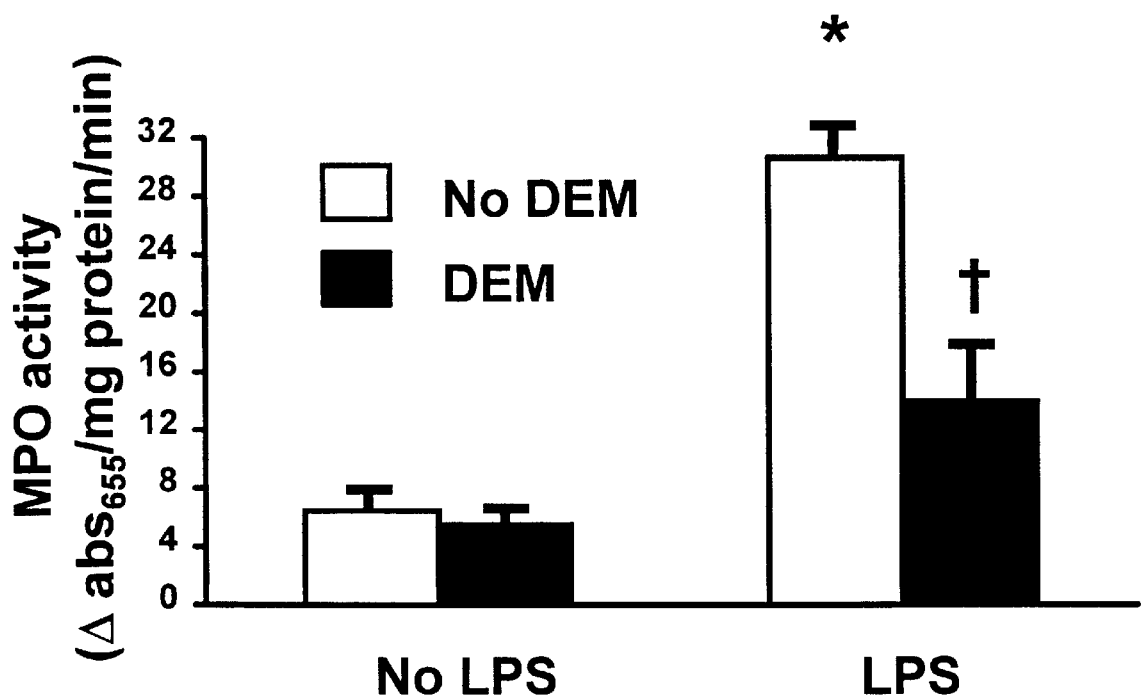
FIG. 16. Effect of DEM on lung PMN influx as assessed by quantitation of total lung myeloperoxidase (MPO) activity. Animals were pretreated with diethylmaleate (6 mmole/kg) or saline one hour prior to Intratracheal endotoxin (500 mg) or vehicle challenge and sacrificed 4 hours later. Data are expressed as mean±SEM of 4–8 animals per group. *$p<0.001$ vs no LPS, no DEM. †$p<0.001$ vs LPS, no DEM, $p<0.01$ vs no LPS, DEM.

We had previously shown reduced numbers of PMN in the bronchoalveolar lavage fluid of animals treated with DEM prior to LPS challenge. Histologic evaluation of lung tissue following LPS treatment in the presence or absence of DEM provided some insight into the mechanism whereby DEM exerted its effect (FIG. 15). LPS challenge causes thickening of the interalveolar septa due to interstitial edema and influx of PMN into the lung Interstitium. By contrast, in animals pretreated with DEM, PMN are absent from both within the alveolar spaces and the interstitium. Further, PMN do not appear to be trapped within the pulmonary capillaries. The reduction in PMN sequestration in the lung is also evident upon evaluation of lung MPO activity. Unlike the quantitation of bronchoalveolar lavage fluid neutrophils, lung MPO activity evaluates total lung PMN content and is a quantitative measure of PMN demonstrated on histologic sections. As shown in FIG. 16, LPS induces a 6-fold increase in lung MPO activity. DEM has no effect on MPO activity in control animals, yet significantly attenuates the increase in lung PMN following LPS challenge. Taken together, these data suggest that DEM prevents LPS-induced PMN sequestration into the lung and the consequent transmigration into the interstitium and alveolar spaces which occurs during lung injury.

Lung PMN sequestration is dependent on interactions between adhesive ligands on the PMN and the pulmonary capillary endothelium. Antibodies directed against $b_2$ integrins or ICAM-1 have been reported to prevent lung PMN influx in a variety of animal models.

EXAMPLE 13
Pretreatment with DEM Attenuates LPS-induced Upregulation of ICAM-1

Figure 17A:
FIG. 17a, b, c. Effect of DEM on lung ICAM-1 expression. Animals were pretreated with diethylmaleate (6 mmole/kg) or saline by intraperitoneal injection one hour prior to intratracheal endotoxin (500 mg) or vehicle challenge and sacrificed 4 hours later. Lungs were fixed by intratracheal instillation of methanotlacetic acid and stained with an anti-ICAM-1 mouse anti-rat mAb as described in methods. Magnification-300×.
Figure 17B:
Figure 17C:

Having previously demonstrated that PMN upregulation of the $b_2$ integrin CD11b/CD18 is unaffected by GSH depletion in this model, we assessed whether pretreatment with DEM attenuated LPS-induced upregulation of its complementary endothelial ligand, ICAM-1. Analysis of lungs obtained from sham animals stained with an anti-ICAM-1 antibody demonstrated low level ICAM-1 expression within the alveolar septa and the epithelial surface (FIG. 17A), a reflection of low level constitutive ICAM-1 expression on the pulmonary capillary endothelium and alveolar epithelial cells, respectively. As demonstrated in FIG. 17B, ICAM-1 expression is markedly upregulated following intratracheal challenge with LPS. By contrast, the upregulation of ICAM-1 expression following LPS challenge was not evident in animals pretreated with DEM (FIG. 17C), suggesting that GSH depletion may be preventing lung leukosequestration through an inhibitory effect on ICAM-1 expression.

Figure 18:
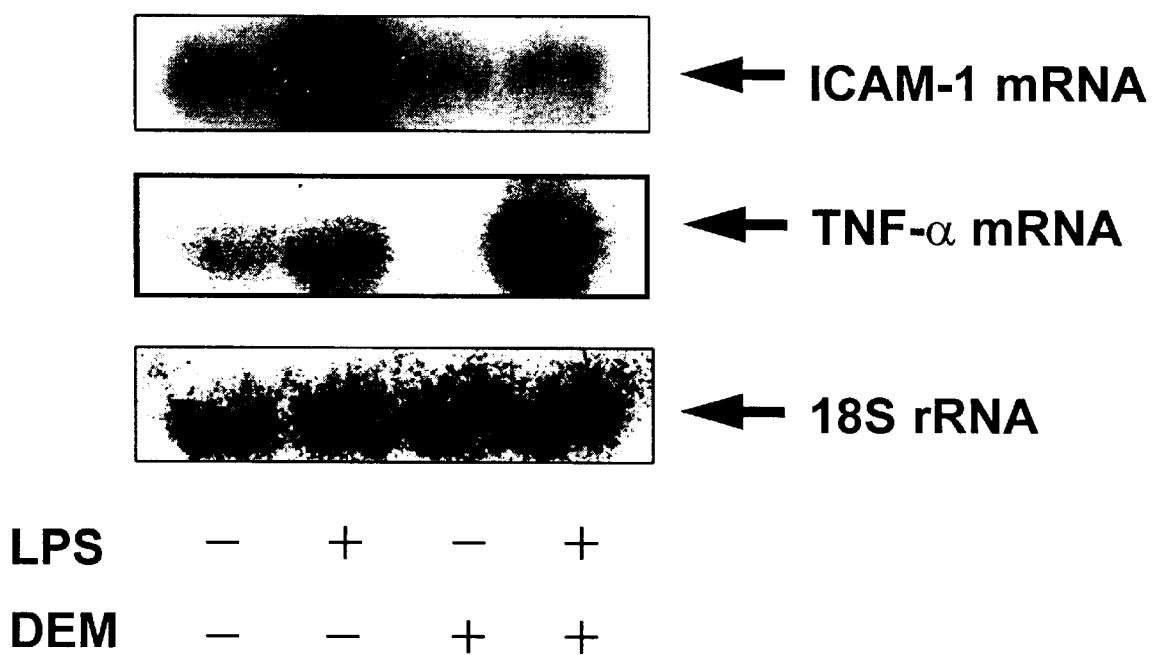
FIG. 18. Effect of DEM on lung ICAM-1 and TNF-a mRNA expression. Animals were pretreated with diethylmaleate (6 mmole/kg) or saline one hour prior to intratracheal endotoxin (500 mg) or vehicle challenge and sacrificed 4 hours later. Total lung RNA was isolated and Northern analysis was performed as described in METHODS. Northern blots were stripped and probed sequentially with ICAM-1, TNF-a, and 18S cDNA probes. Representative study of three separate experiments is demonstrated.

EXAMPLE 14
The Effect of DEM on LPS-induced ICAM-1 Upregulation is Due to Modulation of ICAM-1 Gene Expression To determine whether the observed effect of DEM on LPS-induced ICAM-1 upregulation was due to modulation of ICAM-1 gene expression, we evaluated lung ICAM-1 mRNA expression using northern analysis. As demonstrated in FIG. 18, constitutive ICAM-1 mRNA expression was detectable in whole lungs obtained from control animals. This basal expression was slightly attenuated following DEM pretreatment. In animals receiving LPS there was a significant increase in ICAM-1 mRNA expression, however consistent with its effects on tissue upregulation of ICAM-1 mRNA expression following challenge with LPS. This was not due to a global suppressive effect on gene induction, as lung TNF-a mRNA expression following challenge with LPS in DEM pretreated animals was unaffected.

Figure 19A:
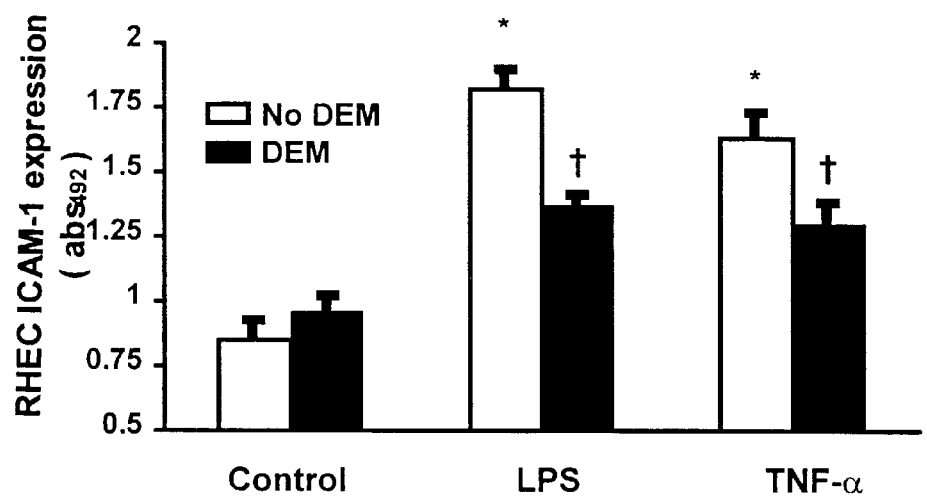
FIG. 19a. Effect of DEM on endothelial ICAM-1 expression in vitro. A) Expression of ICAM-1 on RHEC pretreated with diethylmaleate (250 mM) for 30 minutes prior to addition of either LPS (1 mg/ml) or TNF-a (100 ng/ml) for 6 hours. ICAM-1 expression was determined by ELISA as described in methods. Data are mean±SEM of duplicate wells from 4 experiments. *$p<0.01$ vs control, †$p<0.05$ vs no DEM.
Figure 19B:
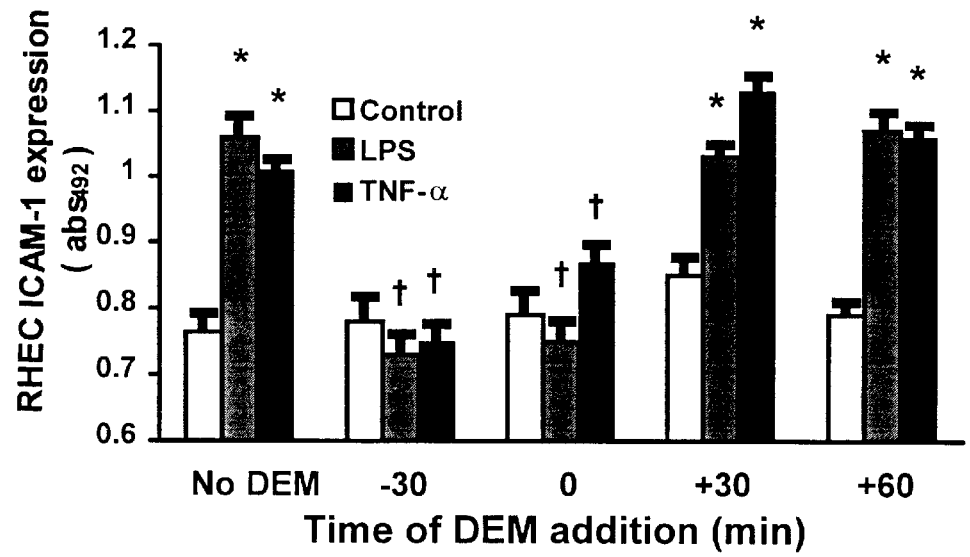
FIG. 19b. Effect of delayed addition of DEM on RHEC ICAM-1 expression. LPS (1mg/ml) or TNF-a (100 ng/ml) were added to the culture medium at time=0. DEM (250 uM) was added from 30 minutes prior (−30) to 60 minutes following (+60) addition of LPS or TNF-a. ICAM-1 expression was evaluated 6 hours following addition of either stimulant. Data are mean±SEM of duplicate wells from 3 experiments. *$p<0.01$ vs control, †$p<0.05$ vs no DEM.
Figure 19C:
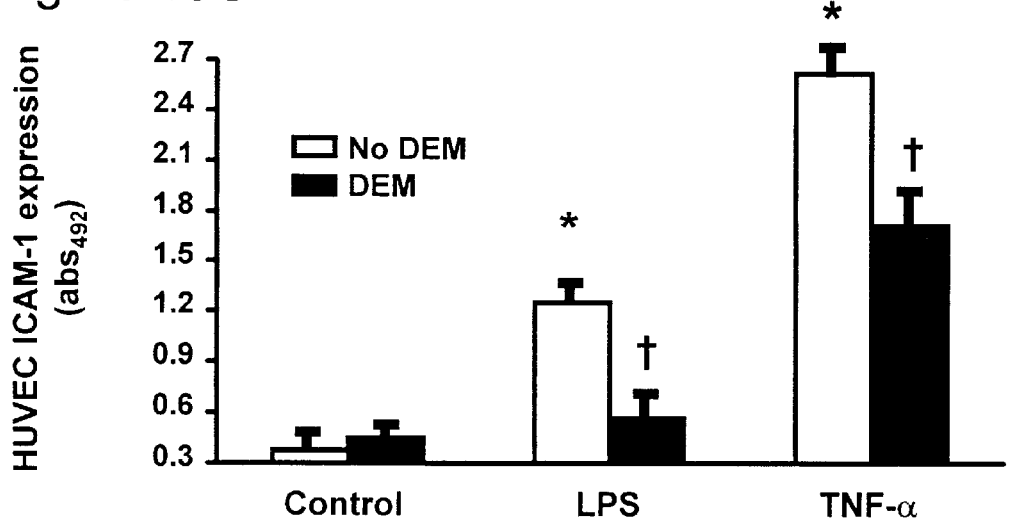
FIG. 19c. Expression of ICAM-1 on HUVEC pretreated with DEM (250 mM) for 30 minutes prior to addition of either LPS (1 mg/ml) or TNF-a (100 ng/ml) for 6 hours. ICAM-1 expression was determined by ELISA as described in methods. Data are mean±SEM of duplicate wells from 3 experiments. *$p<0.01$ vs no LPS, †$p<0.05$ vs no DEM.

EXAMPLE 15
DEM Decreases PMN Sequestration in the Lung by Preventing Endothelial Cell ICAM-1 Upregulation ICAM-1 is expressed on a number of cells present in the lung including endothelial cells, macrophages, neutrophils and alveolar epithelial cells {3224}. Since DEM served to reduced PMN sequestration In the lung, we hypothesized that an effect on endothelial cell ICAM-1 expression might be responsible. To test this possibility, we modeled the system in vitro using RHEC activated by either LPS or TNF-a. In preliminary studies, DEM at 250 mM was sufficient to cause a comparable reduction (≈75%) in intracellular GSH levels (No DEM: 6.74±0.08 vs 1.66±0.1 nmoles/ 106 cells, p<0.01) to that observed in vivo. At this concentration, DEM did not affect cell viability as determined by trypan blue exclusion, nor alter the integrity of the cell monolayer as assessed by permeability to 125I-albumin. Moreover, supernatant lactate dehydrogenase levels were unaffected, demonstrating that DEM was not cytotoxic to the RHEC (Table IV). RHEC treated for 6 hours with either LPS (1 mg/ml) or TNF-a (100 ng/ml) significantly increased ICAM-1 expression (FIG. 19A). Pretreatment with DEM or treatment concomitant with cell stimulation prevented upregulation of ICAM-1 in response to either stimulus (FIG. 19B). DEM did not impair ICAM-1 binding by the primary antibody, as normal levels of ICAM-1 expression were detected with delayed addition (30–60 min) of DEM. To determine whether the effect of GSH depletion on ICAM-1 expression was species specific, this parameter was similarly evaluated in HUVEC. As is evident in FIG. 19C, HUVEC pretreated with DEM, followed by activation with LPS or TNF-a demonstrated a similar attenuation in ICAM-1 upregulation.

TABLE IV

Cytotoxicity of diethylmaleate: RHEC supernatant lactate dehydrogenase activity

| RHEC treatment | Lactate Dehydrogenase Activity (U/L) | |
|---|---|---|
| | No DEM | DEM |
| Control | 43.5 ± 3.5 | 32.5 ± 3.5 |
| LPS (1 mg/ml) | 38.0 ± 1.0 | 33.0 ± 4.0 |
| TNF-a (100 ng/ml) | 40.5 ± 2.5 | 33.5 ± 2.5 |

Data are mean ± SEM of replicate wells from 2 separate experiments.

Figure 20:
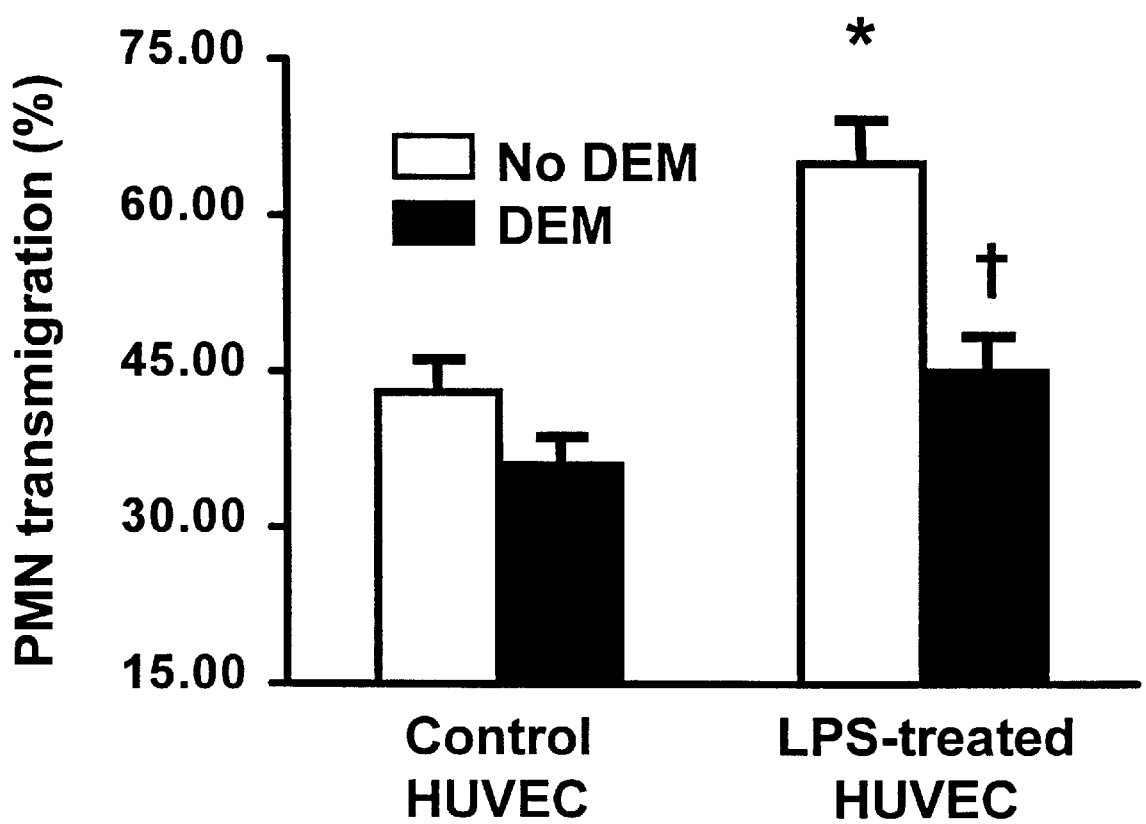
FIG. 20. PMN transendothelial migration across DEM-pretreated HUVEC endothelial monolayers. HUVEC monolayers were grown to confluence on 3 mm pore polycarbonate filters, pretreated with DEM (250 mM) for 30 minutes, followed by activation with LPS (1 mg/ml) for 6 hours. Human PMN transmigration across the monolayers in response to fMLP ($10^{-7}$ M) was assessed as described in methods. Data are mean±SEM of triplicate wells from 3 experiments. *$p<0.05$ vs no LPS. †$p<0.05$ vs no DEM, LPS.

EXAMPLE 16
Reduction in ICAM-1 Expression Mediated by Thiol Depletion Impairs PMN Transmigration Transendothelial migration in vitro is a functional measure of PMN-endothelial cell interactions. To determine whether the reduction in ICAM-1 expression mediated by thiol depletion was sufficient to impair PMN transmigration, we evaluated the effects of endothelial cell thiol depletion on PMN transmigration in vitro. HUVEC monolayers atop a 3 mm pore polycarbonate filter in a dual compartment chamber were pretreated with DEM for 30 minutes followed by activation with LPS (1 mg/ml) for 6 hours. Human peripheral blood neutrophils were then placed atop the monolayer and the rate of transendothelial migration into the bottom chamber in response to fMLP ($10^{-7}$) was evaluated. As shown in FIG. 20, there is an increase in the number of PMN transmigrating across the filter following activation of the endothelium by LPS. By contrast, DEM pretreatment attenuates this increase such that the rate of transmigration is equivalent to that seen under basal conditions. In parallel studies, pretreatment with anti-ICAM-1 antibody resulted in comparable inhibition of transmigration to that observed for DEM (data not shown), suggesting that the reduction in ICAM-1 expression is sufficient to account for the observed effect.

Figure 21:
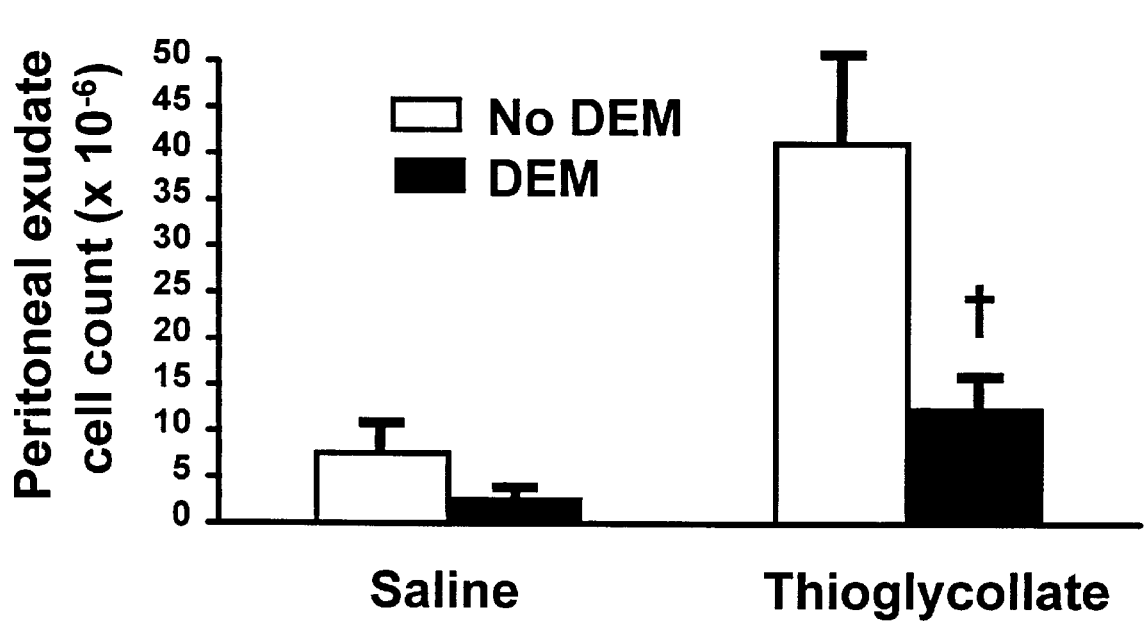
FIG. 21 Effect of DEM on thioglycollate-induced cell influx into the peritoneal cavity. Animals were pretreated with diethylmaleate (6 mmole/kg) or saline one hour prior to administration of thioglycollate or saline (5 ml) by intraperitoneal injection. Animals were sacrificed four hours later. Data are expressed as mean±SEM of 3 animals per group. *$p<0.001$ vs no saline, no DEM. †$p<0.001$ vs thioglycollate, no DEM.
Figure 22:
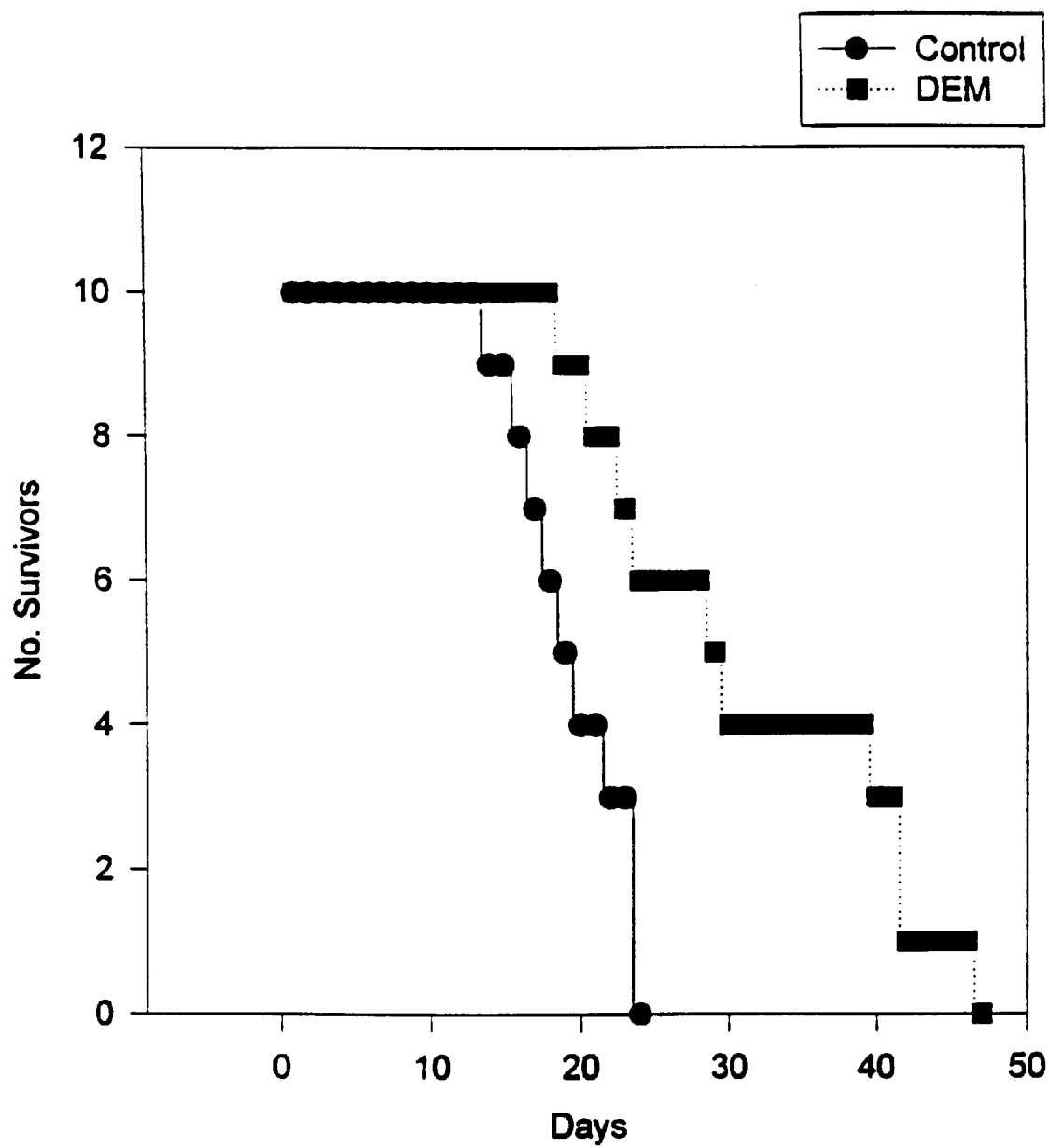
FIG. 22. Effect of DEM on mortality rate of kidney transplant recipients.

EXAMPLE 17
The Effect of GSH Depletion on PMN Trafficking is not Specific to the Pulmonary Microvasculature Antibody strategies aimed at preventing PMN sequestration at various extravascular sites have demonstrated site and stimulus specificity. In the lung, we previously reported that both LPS and IL-1 induced injury were prevented by DEM, suggesting that the effect was not stimulus specific. To determine whether the effect of GSH depletion on PMN trafficking was specific to the pulmonary microvasculature, we evaluated the effect of DEM on thioglycollate-induced PMN influx into the peritoneal cavity. Four hours following the administration of thioglycollate by intraperitoneal injection, the number of peritoneal exudate neutrophils increased from $0.71 \pm 0.9 \times 10^7$ to $4.1 \pm 5.5 \times 10^7$ (p<0.01). This increase was almost completely attenuated by pretreatment with DEM (FIG. 21). DEM had no effect on the basal cell number within the peritoneal cavity.

EXAMPLE 18
DEM Increases Survival Period in Kidney Transplants

A kidney from a black 6 mouse was transplanted into a C3H mouse in a sample of ten test mice and ten control mice. This is a major mismatch. In the test group, donors were given a single injection of DEM (6mmol/kg) immediately prior to the harvest of the kidney. Recipient mice received a single dose prior to insertion of the kidney. No other agents were used. In the control group, donors and recipients were not given an injection of DEM.

The control group recipients had a faster mortality rate. All recipients were dead within 25 days of the kidney transplant. The recipients treated with DEM had a slower mortality rate, with some mice living as long as 40–50 days. Six of the ten recipients treated with DEM were still alive at the time the last recipients in the control group died. The difference is significant at p<0.01 by Chi-squared test (n-10 animals per group).

Material and Methods

Reagents

Escherichia coli 0111:B4 lipopolysaccharide (LPS) was obtained from Difco Laboratories, Detroit, Mich. Murine TNF-a, and human IL-1a were purchased from Genzyme (Cambridge, Mass.). Diethylmaleate (DEM), $PGE_1$, bovine serum albumin (BSA), n-formyl-methionyl-leucyl-phenylalanine (fMLP), phorbol-myristate acetate (PMA), o-phenyldiamine hydrochloride (OPD) and reduced glutathione were all obtained from Sigma Chemical Company (St. Louis, Mo.). 5,5'-dithiobis(2-nitrobenzoic acid) (DTNB) and 5sulfosalicylic acid (SSA) were both purchased from Aldrich Chemical Co. (Milwaukee, Wis.). Neutrophil isolation medium (NIM-2) was obtained from Cardinal Associates (Santa Fe, N.M.). Calcein was purchased from Molecular Probes (Eugene, Oreg.). $^{125}$I-albumin was obtained from Merck Frosst (Montreal, Quebec). Fluorescein isothiocyanate (FITC) conjugated mouse anti-rat CD11b monoclonal antibody (mAb) as well as a FITC conjugated isotypic control murine $IgG_{2a}$ mAb were both purchased from Serotec (Toronto, Canada). Both mouse anti-rat ICAM-1 mAb (clone 1A29) and goat ant-mouse peroxidase-conjugated IgG were a kind gift of Dr. T. Issekutz, University of Toronto. Rabbit anti-mouse biotinylated IgG was used as a secondary antibody for immunohistochemistry and was purchased from Dimension Laboratories (Mississauga, ON). FACS lysing solution was obtained from Becton-Dickinson (San Jose, Calif.). Luminol (5-amino-2,3-dihydro-1,4-phthalazinedione) balanced salt solution (LBSS) was purchased from Exoxemis (San Antonio, Tex.).

Reagents for Examples 11 to 17

Powdered Brewer's thioglycollate and phenolextracted Escherichia coli 0111:B4 LPS were both from Difco Laboratories (Detroit, Mich.). Thioglycollate was dissolved in $H_2O$, autoclaved, and stored in the dark at room temperature until uniformly green and clear. Murine TNF-a was purchased from Genzyme (Cambridge, Mass.). Diethylmaleate (DEM), $PGE_1$, human serum albumin (HSA), o-phenyidiamine hydrochloride (OPD), n-formyl-methionyl-leucyl-phenylalanine (fMLP) and glutathione were all obtained from Sigma Chemical Company (St. Louis, Mo.). Hexadecyltrimethylammonium bromide (HTAB) and phorone (diisopropylidene acetone) were purchased from Fluka (Switzerland). N,N-dimethylformamide was obtained from J.T. Baker Chemical Co. (Phillipsburg, N.J.). 5,5'-dithiobis(2-nitrobenzoic acid) (DTNB) and 5-sulfosalicylic acid (SSA) were both purchased from Aldrich Chemical Co. (Milwaukee, Wis.). $^{125}$I-albumin was obtained from Merck Frosst (Montreal, Quebec) and $Na_2^{51}CrO_4$ from Amersham (Oakville, ON). RPMI and calcium and magnesium free Hanks' balanced salt solution (HBSS) were obtained from GIBCO/BRL Laboratories (Grand Island, N.Y.). Rabbit anti-mouse biotinylated IgG was used as a secondary antibody for immunohistochemistry and was purchased from Dimension Laboratories (Mississauga, ON).

Induction of Acute Lung Injury

Male Sprague Dawley rats weighing 250–275 g were obtained from Charles River Laboratories (Constante, Quebec). All animal studies were performed in accordance with guidelines set forth by the Toronto Hospital Animal Care Committee and the Canadian Council on Animal Care. Animals were housed in standard wire bottom cages, fed standard rat chow and water ad libitum and were allowed to acclimatize before use. Prior to experimentation, animals were fasted overnight and anesthetized with intraperitoneal sodium pentobarbital (50 mg/kg). A tracheostomy was performed and 0.5 ml of saline containing 500 mg of lipopolysaccharide was instilled followed by 20 mechanically ventilated breaths using a rodent ventilator. Sham animals received 0.5 ml of saline alone. Animals were maintained at 37° C. with the use of warming blankets until recovery from anaesthesia.

For examples 11 to 17, systemic GSH depletion in animals was accomplished by administering various doses of DEM or phorone by intraperitoneal injection following an overnight fast Assessment of Lung Injury Pulmonary transcapillary albumin transit was assessed by injection of 1 mCi of $^{125}$I-albumin into the inferior vena cava 30 minutes prior to sacrifice. At the end of the experimental protocol, rats were ventilated, heparin (100 U) was injected into the right ventricle, and 1 ml of blood was withdrawn by cardiac puncture. Following exsanguination, lungs were perfused blood-free by cannulating the pulmonary artery and infusing 10 ml of a low-potassium dextran solution containing 0.5 mg/L of $PGE_1$. The left ventricle, left atria and mitral valve were opened widely to allow free drainage of effluent. The right lung was immediately frozen in liquid nitrogen for assay of non-protein thiols and ICAM-1 and TNF-a mRNA expression, myeloperoxidase activity, as described below. The left lung was used to calculate a permeability index (PI) as follows:

$$PI = \frac{\text{lung cpm/g tissue}}{\text{blood cpm/ml}}$$

Thioglycollate-induced Peritonitis

Male Sprague Dawley rats (250–275 gm) were administered DEM as above, followed one hour later by intraperitoneal injection of thioglycollate (10 ml). Four hours later, animals were sacrificed by carbon dioxide inhalation. Peritoneal exudate cells were obtained following lavage with 60 ml of HBSS. Cell counts were determined using a Coulter counter.

Myeloperoxidase Assay

Lung samples were thawed and approximately 0.2 gm of tissue was homogenized in 25 ml of potassium phosphate (10 mM, pH 7.4) for 1 minute using a Brinkman Polytron (model PT10/35, Brinkman Instruments, Inc., Westburg N.Y.). The homogenate was centrifuged at 12 000 g for 20 min at 4° C. The supernatant was discarded and the pellet was resuspended and homogenized in 25 ml potassium phosphate (50 mM, pH 6.0) containing 0.5% HTAB. The homogenate was frozen overnight at −70° C., rehomogenized for 1 min and sonicated (model VC 50T, Sonics and Materials Inc., CT) at 40 W for 1 min. After centrifugation as above, the supernatant was collected and used for both MPO and protein assay.

MPO activity was assessed at pH 5.4 and 37° C. The change in absorbance at 655 nm during the first three minutes was measured using the Cobas FARA II Chemistry System (Roche Diagnostic Systems, Montclair, N.J.). Each cuvette contained 25 ml of sample, 25 ml of 16 3,3',5,5'-tetramethylbenzidine dissolved in N,N-dimethylformamide and 175 ml of 220 mM potassium phosphate buffer containing 110 mM NaCl. The reaction was initiated by addition of 25 ml of 3.0 mM $H_2O_2$, and the change in absorbance during the first 3 minutes was measured. The absorbance change per min was used as a measure of MPO activity. Results are expressed as MPO activity per mg of protein. Protein concentrations were determined using the Pierce BCA protein assay (Pierce, Rockford, Ill.).

Glutathione Assay

Quantitation of total lung and endothelial non-protein sulfhydryls (NPSH) was assessed using a DTNB based assay as described by Jocelyn. Lung tissue was thawed and weighed, and approximately 0.25 gm was homogenized in 2 ml of 5% SSA. The homogenate was sonicated for 30 seconds and centrifuged for 10 minutes at 10 000 g. The resultant acid thiol extract was assayed for NPSH by quantitating the reduction of DTNB through its conversion to 5-thio-2-nitrobenzoic acid (TNB) at 412 nm using a spectrophotometer. Sample values were then calculated from a standard curve generated using known amounts of GSH and are expressed as GSH equivalents per gram of lung tissue.

Bronchoalveolar Lavage

Bronchoalveolar lavage fluid (BALF) was collected both for cell count and for measurement of tumor necrosis factor alpha (TNF-a). Forty ml of phosphate buffered saline (pH 7.4) was instilled via the trachea in 10 ml aliquots and then gently withdrawn. The first 10 ml of the lavage fluid was centrifuged at 400 g and the cell free supernatant assayed for TNF-a by ELISA. The pellets from individual aliquots were combined and cell counts determined using a Coulter counter.

PMN CD11b Expression

Neutrophil CD11b receptor expression on whole blood PMN was assessed as previously described [16]. Briefly, 100 ml of whole blood was mixed with 10 ml of FITC conjugated anti-CD11b mouse anti-rat mAb or 10 ml of FITC conjugated murine $IgG_2$, isotypic control mAb and incubated for 15 min at 25° C. Red blood cells were lysed with 1 ml FACS lysing solution for 15 min and washed with phosphate buffered saline (PBS). PMN CD11b receptor expression was analyzed on a Coulter EPICS XL-MCL flow cytometer (Coulter Co., Hialeah, Fla.).

Assay of Lung Glutathione

Quantitation of lung non-protein sulfhydryls (NPSH) was assessed using a DTNB based assay as described by Jocelyn [17]. Lung tissue was thawed and weighed, and approximately 0.25 gm was homogenized in 2 ml of 5% SSA. The homogenate was sonicated for 30 seconds and centrifuged for 10 minutes at 10 000 g. The resultant acid thiol extract was assayed for NPSH by quantitating the is reduction of DTNB through its conversion to 5-thio-2-nitrobenzoic acid (TNB) at 412 nm using a spectrophotometer. Sample values were then calculated from a standard curve generated using known amounts of GSH and are expressed as GSH equivalents per gram of lung tissue.

PMN Chemotaxis

Peripheral blood neutrophils were isolated from whole blood by density gradient centrifugation using the NIM-2 rat neutrophil isolation protocol [18]. Viability and purity were routinely in excess of 95% and 80%, respectively. PMN were labelled by resuspension in calcium-magnesium free Hanks balanced salt solution (0.5% BSA, 20 mM HEPES, pH 7.3) containing the acetoxymethyl ester fluorescent probe, calcein (3 mM) and incubated at 37° C. for 30 minutes. Following labelling, the cells were washed in RPMI/10% fetal calf serum and resuspended at $1\times10^6$/ml in PBS/1% BSA. Migration assays were performed in dual compartment chambers separated by a 3 mm pore polycarbonate filter (Corning, Cambridge, Mass.). One hundred thousand cells (100 ml) were placed atop the filter in the upper chamber and 600 ml of RPMI containing the chemotactic stimulus (fMLP, $10^{-8}$ M) in the lower chamber. After incubation for 60 minutes at 37° C., the contents of the lower chamber were collected, pelleted by centrifugation at 400 g×5 minutes, then resuspended in lysis buffer (0.1% SDS, 50 mM Tris, pH 8.5) and transferred to triplicate wells of a 96 well plate. Fluorescence was determined using a fluorescence concentration analyzer (Pandex Laboratories, Mundelein, Ill.). The results are expressed as the percentage of total labelled neutrophils added in the upper chamber that had migrated through the polycarbonate filter.

PMN Chemotaxis (Examples 11 to 17)

Human PMN were isolated from healthy volunteers by collecting blood into heparinized tubes. Neutrophils were Isolated by dextran sedimentation and centrifugation through a discontinuous Ficoll gradient. PMN purity as assessed by size and granularity on flow cytometry was consistently greater than 95%. PMN were labeled with $Na_2{}^{51}CrO_4$ and then resuspended in RPMI 1640 containing 0.5% HSA and 10 mm HEPES (pH 7.4) at a concentration of $10\times10^6$/ml for 30 min and then washed. Transwell chambers with polycarbonate membranes of 3.0 mM pore size (Costar, Cambridge, Mass.) were coated for 1 h with fibronectin (50 mg/ml) and then seeded with $1\times10^5$ HUVEC. Cells were incubated in minimal essential medium with 20% fetal calf serum until confluence as demonstrated by prevention of radiolabelled $^{125}$I-albumin diffusion across the endothelial monolayer. PMN transendothelial migration was assessed as described previously {3682}. Briefly, after treatment of endothelial cells with LPS±DEM, the upper and lower surfaces of the HUVEC-filter units were washed with medium, and then transferred to a new, clean well (lower compartment). To this well, 0.6 ml of RPMI 1640 (10 mM HEPES, pH 7.4, 0.5% HSA) was added containing the chemotactic peptide fMLP ($10^{-7}$ M). Before immersion of the HUVEC-filter unit, 0.1 ml of medium containing $2\times10^5$ labeled PMN was added above the HUVEC. After a 45 min incubation, migration was stopped by washing the upper compartment twice with 0.1 ml of RPMI 1640 to removed nonadherent PMN. The undersurface of the filter was then vigorously rinsed with 2 ml of ice-cold PBS, 0.2% EDTA solution and collected into the lower compartment. The cells that migrated into the lower compartment or that were detached from the undersurface of the filter were lysed by the addition of 0.5% Triton X-100 and analyzed for $^{51}$Cr using a WALLAC 1480 Wizard automatic gamma counter. The results are expressed as the percentage of the total $^{51}$Cr PMN added above the HUVEC monolayer that migrated through the HUVEC-filter unit. All the stimulation conditions were performed with triplicate replicates.

PMN Chemiluminescence

Whole blood chemiluminescence was assessed as previously described [19]. Briefly, 20 ml of blood was obtained via cardiac puncture and added to 400 ml of LBSS. Phorbol ester stimulated chemiluminescence was followed over a 60 minute period using an Automat LB 953 luminometer (Wildbad, Germany). Total chemiluminescence was integrated over this interval using software provided by the manufacturer, and standardized by the number of PMN in the sample of whole blood.

ICAM-1 Immunohistochemistry

At the time of sacrifice, lungs were inflated with approximately 10 ml of methanol/acetic acid (95%:5%) and sections obtained for immunohistochemical analysis. Tissues were stained with anti-rat ICAM-1 mAb, followed by a biotinylated goat anti-mouse IgG. This was followed after rinsing by streptavidin-horseradish peroxidase conjugate. The peroxidase reaction was developed by immersion in a freshly prepared solution of 0.02% 3,3'-diaminobenzidine and 0.005% $H_2O_2$ in 0.05 M Tris buffer, pH 7.6, followed by hematoxylin counterstaining. Appropriate negative controls were performed using secondary antibody alone.

ICAM-1 mRNA Expression

Total RNA from lungs was obtained using the guanidium-isothiocyanate method [20]. Briefly, lungs were harvested from treated animals as described above, and immediately frozen in liquid nitrogen. Lungs were then thawed and homogenized in 10 ml of 4 M guinidine isothiocyanate containing 25 mM sodium citrate, 0.5% sarcosyl, and 100 mM b-mercaptoethanol. RNA was denatured, electrophoresed through a 1.2% formaldehyde-agarose gel, and transferred to nylon membrane. Hybridization was carried out using a $^{32}$P-labeled, random-primed murine ICAM-1 cDNA probe or murine cDNA coding for the 18S ribosomal subunit as previously described [21]. ICAM-1 mRNA expression was quantitated using a phosphoimager (Molecular Dynamics, Sunnyvale, Calif.) and accompanying ImageQuant software. ICAM-1 mRNA expression was standardized to the 18S rRNA signal to compensate for variability in gel loading. For examples 11 to 17, hybridization was carried out using a [a-$^{32}$P]dCTP-labeled, random-primed murine TNF-a, ICAM-1 or IBS ribosomal subunit cDNA probe.

In vitro ICAM-1 Expression

Endothelial cells were isolated from the hearts of 5-day old rats according to the method of Kasten [22] and allowed to grow to confluence. For experiments 11 to 17, human umbilical vein endothelial cells (HUVEC) were isolated as previously described. The endothelial cells were harvested using trypsin-EDTA treatment and seeded into 96 well, flat bottomed microtitre plates in minimal essential medium with 20% fetal calf serum. When the monolayers had reached confluence (approximately 4 days) cells were pretreated with diethylmaleate for 30 minutes followed by activation with either LPS or TNF-a. After 6 hours, supernatants were collected for measurement of lactate dehydrogenase (LDH) activity. Cells were washed twice with RPMI/5% fetal calf serum and incubated with mouse anti-rat ICAM-1 mAb for 1 hour, washed, and then incubated with peroxidase-conjugated goat anti-mouse IgG for 1 hour. Cells were washed again and color development initiated by the addition of the substrate, o-phenyidiamine hydrochloride. After 18 minutes, the reaction was stopped with 3 M sulfuric acid and the optical density at 492 nM determined using a microtitre plate reader. Data are expressed as the change in absorption from baseline. Quantitation of supernatant LDH activity as a measure of cytotoxicity was determined using spectrophotometric methods as previously described [23]. Previous reports have demonstrated that LDH activity is not affected by DEM or other sulfhydryl-reactive agents [24].

Statistical Analysis

Results are expressed as mean±SEM. Statistical significance among the group means was assessed by one-way analysis of variance. Post-hoc testing was performed using the Bonferroni modification of the t-test.

References

1. Sznajder J I, Fraiman A, Hall J B, Sanders W, Schmidt G, Crawford G, et al. Increased hydrogen peroxide in the expired breath of patients with acute hypoxemic respiratory failure. Chest 1989; 96: 606–612.
2. Cochrane C G, Spragg R, Revak S D. Pathogenesis of the adult respiratory distress syndrome: evidence of oxidant activity in bronchoalveolar lavage fluid. J Clin Invest 1983; 71: 754–758.
3. Pacht E R, Timerman A P, Lykens M G, Merola A J. Deficiency of alveolar lining fluid glutathione in patients with sepsis and the adult respiratory distress syndrome. Chest 1991; 100: 1397–1403.
4. Leff J A, Wilke C P, Hybertson B M, Shanley P F, Beehler C J, Repine J E. Postinsult treatment with N-acetylcysteine decreases IL-1 induced neutrophil influx and lung leak in rats. Am J Physiol 1993; 265: L501–L506.
5. Hybertson B M, Leff J A, Beehler C J, Barry P C, Repine J E. Effect of vitamin E deficiency and superficial fluid aerosolized vitamin E supplementation on interleukin-1 induced oxidative lung injury in rats. Free Radic Biol Med 1995; 8–15
6. Suter P M, Domenighetti G, Schaller M-D, Laverriere M C, Ritz R, Perret C. N-acetylcysteine enhances recovery from acute lung injury in man. Chest 1994; 105: 190–194.
7. Knight P R, Druskovich G, Tait A R, Johnson K J. The role of neutrophils, oxidants, and proteases in the pathogenesis of acid pulmonary injury. Anesthesiology 1992; 77: 772–778.
8. Gossage J R, Kuratomi Y, Davidson J M, Lefferts P L, Snapper J R. Neutrophil elastase inhibitors, SC-37698 and SC-39026, reduce endotoxin-induced lung dysfunction in awake sheep. Am Rev Resp Dis 1993; 147: 1371–1379.
9. Kanner S B, Kavanagh T J, Grossmann A, Hu S-L, Bolen J B. Rabinovitch P S, et al. Sulfhydryl oxidation down-regulates T-cell signaling and inhibits tyrosine phosphorylation of phospholipase C-g-1. Proc Natl Acad Sci USA 1992; 89: 300–304.
10. Meyer M, Schreck R, Baeuerle P A. $H_2O_2$ and antioxidants have opposite effects on activation of NF-κB and AP-1 in intact cells: AP-1 as secondary antioxidant-responsive factor. EMBO J 1993; 12: 2005–2015.
11. Malter J S, Hong Y. A redox switch and phosphorylation are involved in the post translational up-regulation of the adenosine-uridine binding factor by phorbol ester and ionophore. J Biol Chem 1991; 266: 3167–3171.
12. Meister A. Glutathione deficiency produced by inhibition of its synthesis, and its reversal: applications in research and therapy. Pharmac Ther 1991; 51: 155–194.
13. Vanella A, Di Giacomo C, Sorrenti V, Russo A, Castorina C, Campisi A, et al. Free radical scavenger depletion in post-ischemic reperfusion brain damage. Neurochem Res 1993; 18: 1337–1340.
14. Tiegs G, Wendel A. Leukotriene-mediated liver injury. Biochem Pharmacol 1988; 37: 2569–2573.
15. Atzori L, Olafsdottir K, Corriga A M, Bannenberg G, Ryrfeldt A, Moldeus P. Thiol modification in $H_2O_2$ and thromboxane induced vas- and bronchoconstriction in rat perfused lung. J Appl Physiol 1991; 71: 1309–1314.
16. Wang J-H, Redmond H P, Watson R W G, Bouchier-Hayes D. Role of lipopolysaccharide and tumor necrosis factor alpha in induction of hepatocyte necrosis. Am J Physiol 1995; 269: G297–G304.
17. Jocelyn PC. Spectrophototemetric assay of thiols. Methods Enzymol 1987; 143: 44–67.
18. Szucs S, Varga C, Ember I, Kertai P. The separation of the granulocytes from different rat strains. J Immunol Methods 1994; 167: 245–251.
19. Allen R C. Phagocytic leukocyte oxygenation activities and chemiluminescence: a kinetic approach to analysis. Methods Enzymol 1986; 133: 449–492.
20. Chomczynski P, Sacchi N. Single step method of RNA isolation by acid guanidium thiocyanate-phenol-chloroform extraction. Anal Biochem 1987; 162: 156

21. Ausubel F M, Brent R, Kingston R E, et al. Current Protocols in Molecular Biology. Green Publishing Associates and Intersciences, 1988: 1–11.
22. Kasten F H. Rat myocardial cells in vitro: mitosis and differentiated properties. In Vitro 1972; 8: 128
23. Bergmeyer H U. Methods of Enzymatic Analysis. New York: Academic Press, 1978: 574–579.
24. Buckley B J, Kent R S, Whorton A R. Regulation of endothelial cell prostaglandin synthesis by glutathione. J Biol Chem 1991; 266: 16659–16666.
25. Mulligan M S, Till G O, Smith C W, Anderson D C, Miyasaka M, Tamatani T, et al. Role of leukocyte adhesion molecules in lung and dermal vascular injury after thermal trauma of skin- Am J Pathol 1994; 144: 1008–1015.
26. Mulligan M S, Vaporciyan A A, Miyasaka M, Tamatani T, Ward P A. Tumor necrosis factor regulates in vivo intrapulmonary expression of ICAM-1. Am J Pathol 1993; 142: 1739–1749.
27. Carlos T M, Harlan J M. Leukocyte-endothelial adhesion molecules. Blood 1994; 84: 2068–2101
28. Horgan M J, Ge M, Gu J, Rothlein R, Malik A B. Role of ICAM-1 in neutrophil-mediated lung vascular injury after occlusion and reperfusion. Am J Physiol 1991; 261: H1678–H1584.
29. Seekamp A, Mulligan M S, Till G O, Smith CW, Miyasaka M, Tamatani T, et al. Role of $b_2$ integrins and ICAM-1 in lung injury following ischemia reperfusion of rat hind limbs. Am J Path 1993; 143: 464–472.
30. Mulligan M S, Vaporciyan A A, Warner R L, Jones M L, Foreman K E, Miyasaka M, et al. Compartmentalized roles for leukocytic adhesion molecules in lung inflammatory injury. J Immunol 1995; 154: 1350–1363.
31. Lo SK, Everitt J, Gu J, Malik A B. Tumor necrosis factor mediates experimental pulmonary edema by ICAM-1 and CD-18 dependent mechanisms. J Clin Invest 1992; 89: 981–988.
32. Xu H, Gonzalo J A, St Pierre Y, Williams I R, Kupper T S, Cotran R S, et al. Leukocytosis and resistance to septic shock in intercellular adhesion molecule 1-deficient mice. J Exp Med 1994; 180: 95–109.
33. Essani N A, Fisher M A, Farhood A, Manning A M, Smith C W, Jaeschke H. Cytokine-induced upregulation of hepatic intercellular adhesion molecule-1 messenger RNA expression and its role in the pathophysiology of murine endotoxin shock and acute liver failure. Hepatol 1995; 21: 1632–1639.
34. Ohh M, Smith C A, Carpenito C, Takei F. Regulation of intercellular adhesion molecule-1 gene expression involves multiple mRNA stabilization mechanisms: effects of interferon-gamma and phorbol myristate acetate. Blood 1994; 84: 2632–2639.
35. Ledebur H C, Parks T P. Transcriptional regulation of the intercellular adhesion molecule-1 gene by Inflammatory cytokines in human endothelial cells. Essential roles of a variant of NF-kappa B site and p65 homodimers. J Biol Chem 1995; 270: 933–943.
36. Wertheimer S J, Myers C L, Wallace R W, Parks T P. Intercellular adhesion molecule-1 gene expression in human endothelial cells. Differential regulation by tumor necrosis factor-alpha and phorbol myristate acetate. J Biol Chem 1992; 267: 12030–12035.
37. Duval D L, Sieg D J, Billings R E. Regulation of hepatic nitric oxide synthase by reactive oxygen intermediates and glutathione. Arch Biochem Biophys 1995; 316: 699–706.
38. Buchmuller-Rouiller Y, Corradin S B, Smith J, Schneider P, Ransijn A, Jongeneel CV, et al. Role of glutathione in macrophage activation: effect of cellular glutathione depletion on nitrite production and leishmanicidal activity. Cell Immunol 1995; 164: 73–80.
39. Rizzardini M, Carelli M, Porras M R C, Cantoni L. Mechanism of endotoxin-induced heme oxygenase mRNA accumulation in mouse liver: synergism by glutathione depletion and protection by n-acetylcysteine. Biochem J 1994; 304: 477–483.
40. Younes M, Robke A. Inhibition of granulocyte mediated release of oxygen free radicals following glutathione depletion. Toxicology Letters 1988; 41: 139–143.
41. Bilzer M, Lauterburg B H. Gluthatione metabolism in activated human neutrophils: stimulation of glutathione synthesis and consumption of glutathione by reactive oxygen species. Eur J Clin Invest 1991; 21: 316–322.
42. Jepsen S, Herlevsen P, Knudsen P, Bud M I, Klausen N-O. Antioxidant treatment with N-acetylcysteine during adult respiratory distress syndrome: a prospective, randomized, placebo controlled study. Crit Care Med 1992; 20: 918–923.
43. Langley S C, Kelly F J. Depletion of pulmonary glutathione using diethymaleic acid accelerates the development of oxygen induced lung injury in term and preterm guinea-pig neonates. J Pharm Pharmacol 1994; 46: 98–102.

References For Example 8

1. Knaus W A, Sun X, Hakim R B, Wagner D P. Evaluation of definitions for adult respiratory distress syndrome. Am J Respir Crit Care Med 1994; 150: 311–7.
2. Inoue S. Nakao A, Kishimoto W, Murakami H. Itoh T, Harada A, Nonami T, Takagi H. Anti-neutrophil antibody attenuates the severity of acute lung injury in rats with experimental acute pancreatitis. Arch Surg 1995; 130: 93–8.
3. Heflin A C, Brigham K L. Prevention by granulocyte depletion of increased vascular permeability of sheep lung following endotoxemia. J Clin Invest 1981; 68: 1253–60.
4. Albelda S M, Smith C W, Ward P A. Adhesion molecules and inflammatory injury. FASEB J 1994; 84: 504–12.
5. Carlos T M, Harlan J M. Leukocyte-endothelial adhesion molecules. Blood 1994; 84: 2068–101.
6. Bauskin A R, Alkalay I, Ben-Neriah Y. Redox regulation of a protein tyrosine kinase in the endoplasmic reticulum. Cell 1991; 66: 685–96.
7. Staal F J T, Roederer M, Herzenberg L A. Intracellular thiols regulate activation of nuclear factor κB and transcription of human immunodeficiency virus. PNAS 1990; 87: 9943–7.
8. Brennan P, O'Neill L A J. Effects of oxidants and antioxidants on nuclear factor kappa B activaiton in three different cell lines: evidence against a universal hypothesis involving oxygen radicals. Biochem Biophys Acta 1995; 1260: 167–75.
9. Schoenberg M H, Beger H G. Reperfusion injury after intestinal ischemia. Crit Care Med 1993; 21: 1376–86.
10. Moore F A, Moore E E. Evolving concepts in the pathogenesis of postinjury multiple organ failure. Surg Clin North Amer 1995; 75: 257–77.
11. Caty M G, Guice K S, Oldham K T, Remick D G, Kunkel S I. Evidence for tumor necrosis factor-induced pulmonary microvascular injury after intestinal ischemia-reperfusion injury. Ann Surg 1990; 212: 694–9.
12. Squadrito F, Altavilla D, Canale P, Ioculano M, Campo G M, Ammendolia L, Squadrito G, Saitta A, Calapai G, Caputi A P. Contribution of intercellular adhesion molecule-1 (ICAM-1) to the pathogenesis of splanchnic artery occlusion in the rat. Br J Pharmacol 1994; 113: 912–6.
13. Fialkow L, Chan C K, Grinstein S, Downey G P. Regulation of tyrosine phosphorylation in neutrophils by the NADPH oxidase. Role of reactive oxygen intermediates. J Biol Chem 1993; 268: 17131–7.
14. Fialkow L, Chan C K, Rotin D, Grinstein S, Downey G P. Activation of the mitogen-activated protein kinase signaling pathway in neutrophils: role of oxidants. J Biol Chem 1994; 269: 1234–42.
15. Schreck R, Rieber P, Baeuerle P A. Reactive oxygen intermediates as apparently widely used messengers in the activation of the NF-kappa B transcription factor and HIV-1. EMBO J 1991; 10: 2247–58.
16. Duval D L, Sieg D J, Billings R E. Regulation of hepatic nitric oxide synthase by reactive oxygen intermediates and glutathione. Arch Biochem Biophys 1995; 318: 699–706.
17. Malter J S, Hong Y. A redox switch and phosphorylation are involved in the post translational up-regulation of the adenosine-uridine binding factor by phorbol ester and ionophore. J Biol Chem 1991; 266: 3167–71.
18. Hwang C, Sinskey A J, Lodish H F. Oxidized redox state of glutathione in the endoplasmic reticulum. Science 1992; 257: 1496–501.
19. Ledebur H C, Parks T P. Transcriptional regulation of the intercellular adhesion molecule-1 gene by inflammatory cytokines in human endothelial cells. Essential roles of a variant NF-kappa B site and p65 homodimers. J Biol Chem 1995; 270: 933–43.
20. Beutler B. Thompson P, Keyes J, Hagerty K, Crawford D. Assay of a ribonuclease that preferentially hydrolyzes mRNAs containing cytokine-derived UA rich instability sequences. Biochem Biophys Acta 1988; 152: 973
21. Gillis P, Malter J S. The adenosine-uridine binding factor recognizes the AU-rich elements of cytokine, lymphokine, and oncogene mRNAs. J Biol Chem 1991; 266: 3172–7.

References for Examples 11–17.

1. Tomashefski, J. F. 1990. Pulmonary pathology of the adult respiratory distress syndrome. *Clinics in Chest Medicine* 11: 593–619.
2. Sznajder, J. I., A. Fraiman, J. B. Hall, W. Sanders, G. Schmidt, G. Crawford, A. Nahum, P. Factor, and L. D. H. Wood. 1989. Increase hydrogen peroxide in the expired breath of patients with acute hypoxemic respiratory failure. *Chest* 96: 606–612.
3. Suter, P. M., S. Suter, E. Girardin, P. Roux-Lombard, G. E. Grau, and J.-M. Dayer. 1992. High bronchoalveolar levels of tumor necrosis factor and its inhibitors, interleukin-1, interferon, and elastase in patients with ARDS after trauma, shock, or sepsis. *Am. Rev. Respir. Dis.* 145: 1016–1022.
4. Mulligan, M. S., G. O. Till, C. W. Smith, D. C. Anderson, M. Miyasaka, T. Tamatani, R. F. Todd, T. B. Issekutz, and P. A. Ward. 1994. Role of leukocyte adhesion molecules in lung and dermal vascular injury after thermal trauma of skin. *Am. J. Pathol.* 144: 1008–1015.
5. Ulich, T. R., S. C. Howard, D. G Remick, E. S. Yi, and et al. 1994. Intratracheal administration of endotoxin and cytokines VIII: LPS induces E-selectin expression. *Inflammation.* 18: 389–398.
6. Winn, R. K., W. J. Mileski, N. L. Kovach, C. M. Doerschuk, C. L. Rice, and J. M. Harlan. 1993. Role of protein synthesis and CD11/CD18 adhesion complex in neutrophil emigration into the lung. *Exp. Lung. Res.* 19: 221–235.
7. Meduri, G. U., G. Kohler, S. Headley, E. Tolley, F. Stentz, and A. Postlethwaite. 1995. Inflammatory cytokines in the BAL of patients with ARDS. *Chest.* 108: 1303–1314.

8. Van Nhieu, J.-T., B. Misset, F. Lebargy, J. Carlet, and J.-F. Bernaudin. 1993. Expression of tumor necrosis factor alpha gene in alveolar macrophages from patients with ARDS. *Am. Rev. Respir. Dis.* 147: 1585–1589.
9. Mulligan, M. S., M. L. Jones, M. A. Bolanowski, and M. P. Baganoff. 1993. Inhibition of lung inflammatory reactions in rats by an anti-human IL-8 antibody. *J. Immunol.* 150: 5585–5595.
10. Rose, C. E., C. A. Juliano, D. E. Tracey, T. Yoshimura, and S. M. Fu. 1994. Role of interleukin-1 in endotoxin-induced lung injury in the rat *Am. J. Respir. Cell. Mol. Biol.* 10: 214–221.
11. Lo, S. K., J. Everitt, J. Gu, and A. B. Malik. 1992 Tumor necrosis factor mediates experimental pulmonary edema by ICAM-1 and CD-18 dependent mechanisms. *J. Clin. Invest* 89: 981–988.
12. Fialkow, L., C. K. Chan, D. Rotin, S. Grinstein, and G. P. Downey. 1994. Activation of the mitogen-activated protein kinase signaling pathway in neutrophils: role of oxidants. *J. Biol. Chem.* 269: 31234–31242.
13. Meyer, M., R. Schreck, and P. A. Baeuerie. 1993. $H_2O_2$ and antioxidants have opposite effects on activation of NF-kappa B and AP-1 in intact cells: AP-1 as secondary antioxidant-responsive factor. *EMBO J.* 12: 2005–2015.
14. Brisseau, G. F., A. P. B. Dackiw, P. Cheung, N. Christie, and O. D. Rotstein. 1995. Posttranscriptional regulation of macrophage tissue factor expression by antioxidants. *Blood* 85: 1025–1035.
15. Hwang, C., A. J. Sinskey, and H. F. Lodish. 1992. Oxidized redox state of glutathione in the endoplasmic reticulum. *Science.* 257: 149–1501.
16. Duval, D. L., D. J. Sieg, and R. E. Billings. 1995. Regulation of hepatic nitric oxide synthase by reactive oxygen intermediates and glutathione. *Arch. Biochem. Biophys.* 316: 699–706.
17. Rizzardini, M., M. Carelli, M. R. C. Porras, and L. Cantoni. 1994. Mechanism of endotoxin-induced heme oxygenase mRNA accumulation in mouse liver: synergism by glutathione depletion and protection by n-acetylcysteine. *Biochem. J.* 304: 477–483.
18. Nathens, A. B., J. C. Marshall, R. W. G. Watson, A. P. B. Dackiw, and O. D. Rotstein. 1996. Diethylmaleate attenuates endotoxin-induced acute lung injury. *Surgery* 120: 360–366.
19. Jocelyn, P. C. 1987. Spectrophototemetric assay of thiols. *Methods. Enzymol.* 143: 44–67.
20. Chomczynski, P. and N. Sacchi. 1987. Single step method of RNA isolation by acid guanidium thiocyanate-phenolchloroform extraction. *Anal, Biochem.* 162: 156–150.
21. Ausubel, F. M., R. Brent, R. E. Kingston, and et al. 1988. Current protocols in Molecular Biology. editor. Green Publishing Associates and intersciences, 1–11.
22. Kasten, F. H. 1972. Rat myocardial cells in vitro: mitosis and differentiated properties. In Vitro 8: 128.
23. Issekutz, A. C., H. E. Chuluyan, and N. Lopes. 1995. CD11/CD18-independent transendothelial migration of human polymorphonuclear leukocytes and monocytes: involvement of distinct and unique mechanisms. *J. Leuk. Biol.* 57: 553–561.
24. Bergmeyer, H. U. 1978. Methods of Enzymatic Analysis. AnonymousAcademic Press, New York. 574–579.
25. Buckley, B. J., R. S. Kent, and A. R. Whorton. 1991. Regulation of endothelial cell prostaglandin synthesis by glutathione. *J. Biol. Chem.* 266: 16659–16666.
26. Watson, R. W., and H. P. Redmond, J. H. Wang, C. Candron, and D. Bouchier-Hayes. 1996. Neutrophils undergo apoptosis following ingestion of *Escherichia coli*. *J. Immunol.* 156: 3986–3992.
27. Issekutz, T. B. and A. Wykretowicz. 1991. Effects of a new monoclonal anti-body, TA-2, that inhibits lymphocyte adherence to cytokine stimulated endothelium in the rat. *J. Immunol.* 147: 109–116.
28. Tang, W. W., E. S. Yi, D. G. Remick, A. Wittwer, S. Yin, M. Qi, and T. R. Ulich. 1995. Intratracheal injection of endotoxin and cytokines. IX. Contribution of CD11a/ICAM-1 to neutrophil emigration. *Am. J. Physiol.* 269: L653–L659.
29. Seekamp, A., M. S. Mulligan, G. O. Till, C. W. Smith, M. Miyasaka, T. Tamatani, R. F. Todd, and P. A. Ward. 1993. Role of beta-2 integrins and ICAM-1 in lung injury following ischemia reperfusion of rat alveolar epithelial cells. *Am. J Respir. Cell. Mol. Biol.* 8: 9–15.
30. Christensen, P. J., S. Kim, H. Simon, G. B. Toews, and R. Paine. 1993. Differentiation-related expression of ICAM-1 by rat alveolar epithelial cells. *Am. J. Respir. Cell. Mol. Biol.* 8: 9–15.
31. Carlos, T. M. and J. M. Harlan. 1994. Leukocyte-endothelial adhesion molecules. *Blood.* 84: 2068–2101.
32. Ohh, M., C. A. Smith, C. Carpenito, and F. Takei. 1994. Regulation of intercellular adhesion molecule-1 gene expression involves multiple mRNA stabilization mechanisms: effects of interferon-gamma and phorbol myristate acetate. *Blood.* 84: 2632–2639.
33. Ledebur, H. C. and T. P. Parks. 1995. Transcriptional regulation of the intercellular adhesion molecule-1 gene by inflammatory cytokines in human endothelial cells. Essential roles of a variant NF-kappa B site and p65 homodimers. *J. Biol. Chem.* 270: 933–943.
34. Galter, D., S. Mihm, and W. Droge. 1994. Distinct effect glutathione disulfide on the nuclear transcription factors kappa B and activator protein-1. *Eur. J. Biochem.* 221: 639–648.
35. Chen, C.-Y. A. and A.-B. Shyu. 1995. AU-rich elements: characterization and importance in mRNA degradation. *Trends. Biochem. Sci.* 20: 465–470.
36. Malter, J. S. and Y. Hong. 1991. A redox switch and phosphorylation are involved in the post translational up-regulation of the adenosine-urdine binding factor by phorbol ester and ionophore. *J. Biol. Chem.* 266: 3167–3171.
37. Buchmuller-Rouiller, Y., S. B. Corradin, J. Smith, P. Schneider, A. Ransijn, C. V. Jongeneel, and J. Mauel. 1995. Role of glutathione in macrophage activation: effect of cellular glutathione depletion on nitrate production and leishmanicidal activity. *Cell. Immunol.* 164: 73–80.
38. Edwards, B. S., M. C. Curry, E. A. Southon, M. Kutny, and J. L. Born. 1996. Redox interactions alter LFA-1 conformation, cytoskeleton linkage and adhesion. *FASEB. J.* 10: A1202. (Abstract)
39. Vanella, A., C. Di Giacomo, V. Sorrenti, A. Russo, C. Castorina, A. Campisi, M. Renis, and J. R. Perez-Polo. 1993. Free radical scavenger depletion in post-ischemic reperfusion brain damage. *Neurochem Res* 18: 1337–1340.
40. Tiegs, G. and A. Wendel. 1988. Leukotriene-mediated liver injury. *Biochem. Pharmacol.* 37: 2569–2573.
41. Suter, P. M., Domenighetti, M.-D. Schaller, M. C. Laverriere, R. Ritz, and C. Perret. 1994. N-acetylcysteine enhances recovery from acute lung injury in man. *Chest* 105: 190–194.
42. Jepson, S., P. Herlevsen, P. Knudsen, M. I. Bud, and N.-O. Klausen. 1992. Antioxidant treatment with N-acetylcysteine during adult respiratory distress syndrome: a prospective, randomized, placebo controlled study. Crit. Care. Med. 20: 918–923.

We claim:

1. A method of reducing or inhibiting inflammation and inducing or promoting anti-pyresis, comprising administeting to a mammal in need of such treatment an amount of a glutathione (GSH) depleting agent effective to reduce or inhibit neutrophil sequestration at the inflammation site.

2. The method of claim 1, wherein the GSH depleting agent is selected from the group consisting of diethylmaleate (DEM), thiol depleting DEM mimetics, phorone, thiol depleting phorone mimetics, buthioninc sulfoximine (BSO), and thiol depleting BSO mimetics.

3. The method of claim 2, wherein the agent is selected from a group consisting of diethylmaleate (DEM), phorone and buthionine sulfoximine (BSO).

4. The method of claim 2, wherein the GSH depleting agent is selected from a group consisting of diehylmaleate (DEM), phorone and buthionine sulfoximine (BSO) mimetics.

5. The method of claim 1, wherein the agent is administered orally, parenterally, cavitarily, rectally or through an air passage.

6. The method of claim 1, wherein the agent is administered before, during or after initiation of the process leading to the neutrophil-endothelial cell interaction.

7. The method of claim 1, wherein the agent is selected from the group consisting of diethylmaleate (DEM), phorone, buthionine-sulfoximine (BSO), a glutathione depleting diethylmaleate (DEM) mimetic, a glutathione depleting phorone mimetic, a glutathione depleting buthionine sulfoximine (BSO) mimetic; and is administered as a pharmaceutical composition comprising the GSH depleting agent and a slow release carrier.

8. The method of claim 7, wherein the slow release carrier comprises liposomes.

9. The method of claim 7, wherein the composition further comprises an additive selected from the group consisting or aggregants, disaggregants, osmotic pressure regulating salts, buffers, sweeteners and coloring agents.

10. The method of claim 7, wherein the composition is administered as a formulation selected from the group consisting of tablets, dragees, capsules, granules, suppositories, solutions, suspensions and lyophilized compositions.

11. The method of claim 8, wherein the composition is in injectable form, and comprises a lyophilized composition and a liquid carrier.

12. The method of claim 7, wherein the carrier is selected from the group consisting of solid or liquid inert diluents.

13. The method of claim 1, wherein the amount of the GSH depleting agent administered is effective to reduce or inhibit neutrophil-endothelial cell adhesion at the site of inflammation.

14. The method of claim 1, wherein the amount of the GSH depleting agent administered is effective to reduce or inhibit the production or level of at least one adhesion molecule produced by endothelial cells at the site of inflammation.

15. The method of claim 1, wherein the amount of the GSH depleting agent administered to reduce or inhibit the binding of neutrophils to endothelial cells at the inflammation site is effective to reduce or inhibit the production or level of a molecule selected from the group consisting of $\beta 2$ integrins, ICAM-1, VCAM, PECAM, procoagulant tissue factor, NF-κB and E-selectin.

16. The method of claim 1, wherein the reduction of neutrophil sequestration is effective to reduce or inhibit the secretion of endothelial cell-damaging toxic molecules by neutrophils.

17. The method of claim 1, wherein the amount of the agent administered is effective to reduce or inhibit the production and/or level of a molecule selected from the group consisting of $\beta 2$ integrins, ICAM-1, VCAM, PECAM, procoagulant tissue factor, NF-κB and E-selectin.

18. The method of claim 1, wherein the reduction of neutrophil-endothelial cell interaction by the agent prevents the secretion by neutrophils of endothelial cell-damaging toxic molecules.

19. A method of treating a disease or condition associated with inflammation other than ischemia, comprising administering to a mammal in need of such treatment an amount of a glutathione (GSH) depleting agent effective to reduce or inhibit neutrophil sequestration at the inflammation site.

20. The method of claim 19, wherein the disease or condition is selected from the group consisting of diseases or conditions of the lung, skin, articulations, liver, extremities, intestine, gastrointestinal tract, kidney, endothelium, heart, umbilicum, veins, capillaries, arteries, vasculature and peritoneal cavity.

21. The method of claim 19, wherein the disease or condition is selected from the group consisting of revascularization, trauma, injury, transplantation, infection, reperfusion injury, acute synovitis, myo-cardial infarction, post-infarction, reinfarction, arthritis, post-ischemia and stroke.

22. The method of claim 21, wherein the disease or condition is arthritis.

23. The method of claim 22, wherein the disease or condition is rheumatoid arthritis.

24. The method of claim 19, wherein the disease or condition of the lung is acute lung injury.

25. The method of claim 19, wherein the disease or condition is respiratory failure.

26. The method of claim 25, wherein the respiratory failure is acute respiratory distress syndrome (ARDS).

27. The method of claim 20, wherein the disease or condition is liver injury.

28. A method of preventing mortality resulting from a disease or condition associated with inflammation or pyresis, comprising conducting the method of claim 19.

* * * * *